US009387279B2

(12) United States Patent
Wu et al.

(10) Patent No.: US 9,387,279 B2
(45) Date of Patent: Jul. 12, 2016

(54) IMPLANTABLE-GLUCOSE RESPONSIVE INSULIN DELIVERY DEVICE

(71) Applicant: The Governing Council of the Univeristy of Toronto, Toronto (CA)

(72) Inventors: Xiao Yu Wu, Toronto (CA); Kai Zhang, Brampton (CA); Huiyu Huang, Toronto (CA); Claudia Gordijo, Toronto (CA); Jason Siu-Wei Li, Toronto (CA); Michael K.L. Chu, Toronto (CA)

(73) Assignee: The Governing Council of the University of Toronto, Ontario (CA)

( * ) Notice: Subject to any disclaimer, the term of this patent is extended or adjusted under 35 U.S.C. 154(b) by 25 days.

(21) Appl. No.: 14/230,971

(22) Filed: Mar. 31, 2014

(65) Prior Publication Data
US 2014/0213963 A1    Jul. 31, 2014

Related U.S. Application Data

(63) Continuation-in-part of application No. 13/101,634, filed on May 5, 2011, now Pat. No. 8,702,645.

(60) Provisional application No. 61/331,690, filed on May 5, 2010.

(51) Int. Cl.
*A61M 31/00* (2006.01)
*A61L 31/04* (2006.01)
*A61M 5/142* (2006.01)

(52) U.S. Cl.
CPC .......... *A61L 31/041* (2013.01); *A61M 5/14276* (2013.01); *A61M 2205/0227* (2013.01); *A61M 2230/201* (2013.01)

(58) Field of Classification Search
CPC ............... A61M 2205/0227; A61M 2230/201; A61M 5/14276
USPC ............................ 604/503, 890.1, 891.1, 66; 424/424–426
See application file for complete search history.

(56) References Cited

U.S. PATENT DOCUMENTS

| 5,226,902 A | 7/1993 | Bae et al. |
|---|---|---|
| 6,565,872 B2 | 5/2003 | Wu et al. |
| 6,858,406 B1 | 2/2005 | Vrlijc et al. |
| 8,702,645 B2 * | 4/2014 | Wu .................. A61M 5/14276 424/424 |

OTHER PUBLICATIONS

Gordijo et al. "A New Bio-Inorganic Nanocomposite Membrane for Glucose-Modulated Release of Insulin," MRS Symposium Proceedings (Dec. 2009) (poster).

(Continued)

*Primary Examiner* — Kevin C Sirmons
*Assistant Examiner* — Deanna K Hall
(74) *Attorney, Agent, or Firm* — Cesari and McKenna LLP

(57) ABSTRACT

A biocompatible insulin delivery device is provided comprising an insulin reservoir sealed with a glucose-responsive plug or membrane. The plug functions to release insulin from the reservoir in response to a hyperglycemic glucose concentration and to prevent insulin release from the reservoir in response to hypoglycemic glucose concentration. In one embodiment, the plug is made of a biocompatible polymeric matrix comprising an inorganic component, a stimulus-responsive component and a catalytic component.

17 Claims, 20 Drawing Sheets

(56) References Cited

OTHER PUBLICATIONS

Gordijo et al. "Closed Loop Insulin Delivery Device: Fabrication in vitro and in vivo Evaluation of Self-Regulated Insulin Release," Diabetes Technology Soc. Annual Meeting (Nov. 2009) (poster).

Gordijo et al. "Glucose-Responsive Bioinorganic Nanohybrid Membrane for Self-Regulated Insulin Release," Adv. Func. Matter., 20:1-9 (2010).

Gordijo et al. "Nanofunctionalized Glucose-Responsive Implantable Devise for Self-Regulated Insulin Release," MRS Functionalized Nanobiomaterials for Medical Applications (Oct. 2010) (oral presentation).

* cited by examiner a)

b)

a)

b)

a)

b)

IMPLANTABLE-GLUCOSE RESPONSIVE INSULIN DELIVERY DEVICE

CROSS-REFERENCE TO RELATED APPLICATIONS

This application is a Continuation in Part of U.S. application Ser. No. 13/101,634 filed on May 5, 2011, now U.S. Pat. No. 8,702,645, which claims the benefit of U.S. Provisional Application No. 61/331,690 filed on May 5, 2010. The contents of both applications are hereby incorporated by reference in their entirety.

FIELD OF THE INVENTION

The present invention relates generally to the field of insulin delivery, and in particular, to a glucose responsive insulin delivery device.

BACKGROUND OF THE INVENTION

Diabetes is a serious medical condition characterized by the body's inability or deficiency to metabolize glucose. This disease affects almost 250 million people worldwide and is the $4^{th}$ leading cause of death globally. The number of diabetes patients is expected to increase to at least 300 million in 2025. There are two major types of diabetes mellitus: Type 1 diabetes, caused by insufficient secretion of insulin due to the damage of pancreatic beta cells, which requires frequent administration of exogenous insulin to sustain life; and Type 2 diabetes, often caused by inadequate endogenous insulin to control glucose levels, which is currently managed through dietary modifications, exercise, medication, or through insulin injections in about 20% of the cases. In both types of diabetes, hypoglycemia frequently results from the use of insulin, owing to a very poor approximation of normal physiological insulin secretion that is tightly modulated by glucose levels. In order to maintain blood glucose levels within the normal range, diabetic patients have to administer insulin periodically prior to meals or when it is needed as indicated by self-examination of blood glucose levels. This process is painful, inaccurate, inconvenient, and cannot monitor and deliver necessary insulin at night during sleep. Therefore, research has been conducted actively in past decades to explore better ways of monitoring glucose concentration and delivering insulin continuously and automatically. Unfortunately, development of glucose-responsive insulin delivery systems has still been unsatisfactory, though a few glucose sensors have been or are being developed. In addition, linking the sensor with the insulin pump has been attempted.

Different approaches to insulin delivery have been investigated including delivery of insulin via oral, nasal, or pulmonary routes and transplantation of islet cells. Except for the latter approach, other treatment options cannot provide automatic supply of insulin when needed. Transplantation of pancreatic islet cell into patients was conducted in multicenter clinical trials of Edmonton Protocol (Canada) and showed great promise of normalizing a patient's pancreatic functions. However, because of chronic use of immunosuppressive drugs, limited sources of the cells (only sufficient islets from donors to treat 0.1% of the true need in type 1 diabetes), and the high cost of the treatment ($140K per patient), renders this approach unavailable to the majority of patients. Moreover, to date, long-term function of the transplanted islets has been difficult to accomplish with only 10% of patients maintaining insulin independence 5 years after transplantation. Even for those patients receiving islet cell transplant, interim insulin treatment is necessary to preserve the function of the islet cells at the outset.

Animals, just like humans, can acquire Type 1 or Type 2 diabetes. Canine diabetes is an endocrine disorder which is seen in pets such as cats and dogs and in big animals like horses. Diabetes in animals requires daily management and, in most cases, treatment by owners. In this case, the burden and difficulty of administering treatment and the costs associated with treatment rests on the pet/animal owners. Type I diabetes in animals occurs when there is a lack of insulin production and secretion by the pancreas. This form is identified in approximately 50 to 70% of cats diagnosed with diabetes mellitus, and requires insulin injections to control the disease. Most cats will require one or two daily injections of insulin to control blood glucose. Diabetic dogs almost always (99%) have Type I diabetes and also require one or two daily injections of insulin. The injections are given under the skin using a small needle. Dogs tend to get diabetes early in life. For instance, juvenile-onset diabetes (Type 1) may occur in dogs at less than 1 year of age. Although cats tend to get diabetes later in life, e.g. middle-aged to older, it may also occur in cats younger than 1 year of age.

Type II diabetes occurs when enough insulin is produced but something interferes with its ability to be utilized by the body. This form is identified in approximately 30% of cats with diabetes mellitus. In order to maintain blood glucose levels within the normal range, diabetic animals need to have insulin administered periodically prior to meals or when it is needed as indicated by glucose level examination. As animals cannot do this for themselves, owners have to make sure that their animals are getting the proper treatments at very specific times. The process is painful and uncomfortable for the animals, can be inaccurate and inconvenient, and is clearly a burden on a pet owner.

Numerous groups have attempted to develop closed-loop insulin delivery systems (SRIDS). The principle of SRIDS is to integrate a sensing element and a responsive release mechanism into one system. In addition to the biological approach, i.e., islet cell transplantation, electromechanical and physiochemical approaches have been investigated. In the electromechanical approach, an insulin pump infuses insulin controlled by a computer that receives signals from a glucose sensor. However, to date, no integrated closed-loop insulin pump system is available for human use. Currently available insulin pumps deliver insulin continuously and subcutaneously or intraperitoneally in the case of the external pumps. In 2006 a sensor-augmented pump, the Mini-Med Paradigm® REAL-Time System (Medtronic Diabetes, California) received FDA approval. This system consists of a CGMS Guardian RT glucose monitor and an insulin pump. Although this system can offer better control of blood glucose levels than periodic injections, it is not a closed-loop system. It provides real-time information about carbohydrate count and historical data based on which pump settings can be adjusted by users thus achieving better control of glucose levels. Integrated systems are also being investigated using microdialysis, subcutaneous or intravenous sensors, together with implanted pump or external pump.

While significant progress has been made to close the loop between glucose sensor and insulin delivery pump, this electromechanical approach is not without problems. For example, insulin pumps were recalled due to patient injuries and even deaths associated with use of the pumps. Transmission of blood sugar signals to the pump via radio frequency may interfere with cell phones or radio traffic giving problems inside airplanes. Moreover, the users still need to conduct finger pricking measurements for calibrating the sensors every 24 or 48 hours.

Physicochemical approaches to the development of SRIDS utilize physical interactions or chemical reactions that trigger changes in polymer properties allowing more or less insulin to be delivered. Similar to the principal mechanism of most glucose sensors, glucose oxidation by glucose oxidase (GOx) is used to generate pH or hydrogen peroxide signals. Polymers containing amino groups swell at lower pH in response to higher glucose levels allowing more insulin to be released either by creating larger pores or by pushing insulin solution out. The disadvantages of such an approach include slow response of the bulk hydrogels, weak mechanical strength, and possible binding of negatively charged insulin with positively charged polymers hindering insulin release. Carboxyl group-containing polymers, e.g. poly(acrylic acid), were grafted onto a porous membrane/filter and used to regulate insulin release by glucose oxidation. This method offered a faster response and higher mechanical strength than the bulk hydrogel, however, it resulted in very low enzyme immobilization and difficult control of surface grafting. Redox polymers have been applied with glucose oxidation, however, hydrogen peroxide is produced. The polymers changed from reduced form (hydrophobic) to oxidized form (hydrophilic), thus increasing the permeability of insulin through the polymer. This method suffers a very small change (<1.5-fold increase) in insulin permeability as glucose concentration was raised from zero to 5,000 mg/dL, which is unrealistically high as compared to 200-400 mg/dL, hyperglycemia levels in the body.

Competitive binding of glucose with sugar ligands and competitive binding of glucose with polymers are other physicochemical approaches. Glycosylated insulin forms a complex with lectin. As free glucose diffuses into the complex, the glycosylated insulin is replaced and released out. This binding mechanism is non-specific because other endogenous sugars can also bind with lectin, resulting in false signals. Competitive binding of free glucose with polymers is also used to induce polymer swelling or dissolving, thus increasing insulin release. This method is also problematic because other diols or sugars in the body can bind to boronic acid and concanavalin-A.

In view of the foregoing, it is evident that there is a need to develop alternative ways of treating diabetes, in both humans and animals, that allow for effective and accurate treatment.

SUMMARY OF THE INVENTION

A closed-loop implantable insulin delivery device has now been developed that functions to control insulin release continuously and automatically in vivo in response to blood glucose levels.

In one aspect of the invention, a biocompatible insulin delivery device is provided comprising an insulin reservoir sealed with a glucose-responsive plug or membrane, wherein the plug or membrane functions to release insulin from the reservoir in response to a hyperglycemic glucose concentration and to prevent insulin release from the reservoir in response to hypoglycemic glucose concentration.

In another aspect of the invention, a biocompatible glucose-responsive membrane is provided that comprises a polymeric matrix having an inorganic component and a stimuli-responsive component adapted to alter the porosity of the matrix in response to a change in glucose concentration.

In a further aspect, a method of treating diabetes is provided comprising implanting a biocompatible insulin delivery device into the mammal, wherein the device comprises an insulin reservoir sealed with a glucose-responsive plug or membrane, wherein the plug or membrane functions to release insulin from the reservoir in response to a hyperglycemic glucose concentration and to prevent insulin release from the reservoir in response to hypoglycemic glucose concentration.

These and other aspects of the present invention will become apparent from the following detailed description by reference to the figures. It should be understood, however, that the detailed description and the specific examples while indicating preferred embodiments of the invention are given by way of illustration only, since various modifications and changes within the spirit and scope of the invention will become apparent to those skilled in the art from this detailed description.

DETAILED DESCRIPTION OF THE INVENTION

A biocompatible insulin delivery device is provided comprising an insulin reservoir capped with a glucose-responsive membrane or plug. The membrane/plug functions to release insulin from the reservoir in response to a hyperglycemic glucose concentration and to prevent insulin release from the reservoir in response to a hypoglycemic glucose concentration. Thus, integration of the glucose-responsive membrane or plug with the insulin reservoir provides a device that enables continuous sensing of glucose levels in real-time and corresponding automatic adjustment of insulin release rate.

Figure 1A:
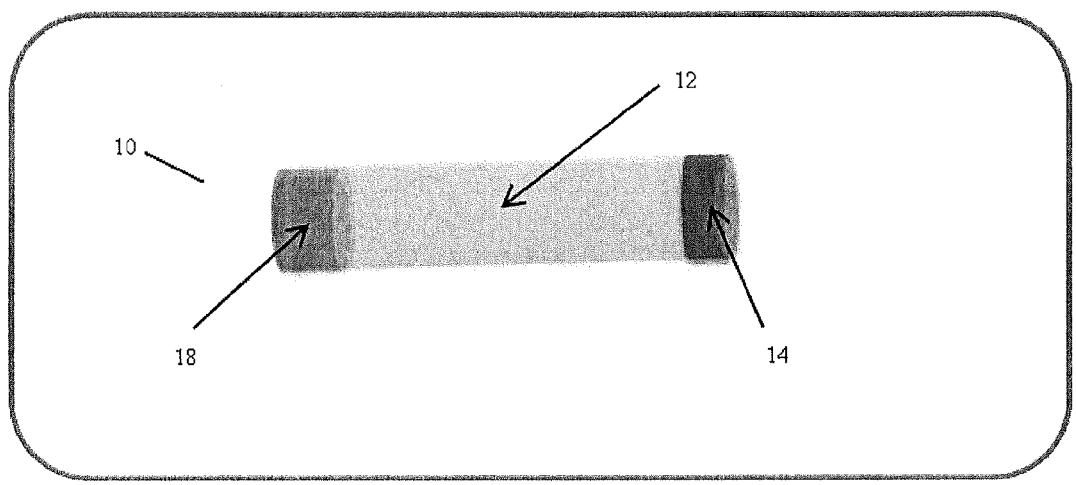
FIG. 1 is a schematic showing an insulin delivery device in accordance with an embodiment of the invention (A), and the mechanism of the glucose-responsive release of insulin across the plug (B)
Figure 1B:
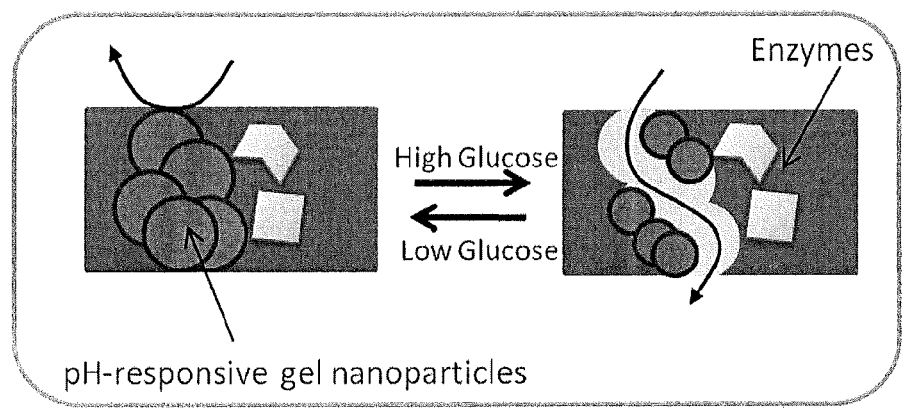

An insulin delivery device (10) in accordance with the invention is shown in FIG. 1A, comprising an insulin reservoir (12) and a glucose-responsive plug (14). If the body of the reservoir (12) is open-ended (as in the case of a tube), it may include sealing (16) at the open end thereof. Materials appropriate for such sealing include, but are not limited to, biocompatible metallic materials, inorganic materials comprising glass and ceramic, and polymers. Suitable polymers include polyvinyls, polyamides, polyurethanes, silicon rubbers and acrylic polymers. Examples of such polymers include poly(ethylene-co-vinyl acetate), ethylcellulose, silicone rubber and polydimethylsiloxane.

The reservoir of the device is in a form suitable to retain insulin, e.g. a tube or disk, having an opening suitable to receive the insulin-release glucose-responsive plug or membrane. The reservoir may be made of any biocompatible material, or material altered to become biocompatible, that is suitable to retain insulin. Thus, the reservoir may be made of synthetic or natural polymers such as collagen, starch blends, hyaluronic acid, alginates, carrageenan, silicone rubbers, polydimethylsiloxane (PDMS), polyurethanes, acrylic polymers, poly(methyl methacrylate), polyesters, cellulose derivatives, cellulose acetate, polyethylene terephthalate, polycarbonate, polysulfone, polyvinyl chloride, polyethylene, polypropylene, polymethylacrylate and nylon. The reservoir may also be made of biocompatible metals, glass, ceramics, or hybrid materials formed with a biocompatible metal, glass or ceramics with one or more polymers. The surface of the device may additionally be functionalized to improve the safety, hydrophilicity and biocompatibility of the device, to improve adherence of the device to a plug or membrane and/or to avoid aggregation of insulin within the interior of the reservoir that may be induced by hydrophobic surfaces. Advanced surface modification techniques (e.g. silanization and PEGylation) may be applied to achieve one or more of these improvements.

The surface of the device and the membrane or plug may be modified with a non-fouling material that prevents cell adhesion. The non-fouling material may be covalently or physically bound to the surface of the device. Examples of non-fouling materials include hydrophilic polymers comprising polyethylene glycol (PEG) chains of various molecular weights, and hydrophobic polymers comprising poly(ethylene-co-vinylacetate). The polymer layers may contain polyelectrolytes and immunomodulators comprising heparin and anti-inflammatory peptides. For example, surface modification of the device with hydrophilic polymers such as PEG of at least about 2 kDa, for example, about 2-50 kDa, preferably at least about 10 kDa, for example, at least about 20 kDa or greater, may advantageously improve biocompatibility of the device, minimizing tissue encapsulation, inflammation and immune responses on implantation.

The glucose-responsive plug may optionally be covered by a protective, biocompatible microporous membrane to reduce the inflammatory response and fibrous buildup at the plug surface, thereby improving biocompatibility and reducing implant degradation. The protective membrane may be made of biocompatible polymers such as, but not limited to, polyvinyls, polyamides, polyimides, polysulphones, polyurethanes, polyolefins, polyesters, polycarbonates, polyacrylates, polysaccharides, poly(amino acids), silicone rubbers and acrylic polymers. Examples of such polymers include poly(vinyl chloride), poly(vinyl acetate), poly(ethylene-co-vinyl acetate) (EVA), poly(ethylene), poly(propylene), poly(lactic-co-glycolic acid) (PLGA), poly(methyl methacrylate) (PMMA), ethylcellulose, cellulose acetate, cellulose nitrate, aramids, nylons, polybutylene and ethylene propylene rubbers, and poly(dimethylsiloxane) (PDMS).

The protective membrane includes pores of sufficient size to permit release of insulin from the device, while preventing or at least minimizing access of inflammatory cells and fibrous material to the plug surface. Pores may range in size from about 5-100 μm, preferably 10-50 μm, e.g. 10-30 μm such as 10-20 μm. In a further embodiment, the protective membrane is spaced from the plug surface, e.g. the plug is positioned within the device such that there is a space or gap between the plug surface and the protective membrane which seals or covers the device reservoir at the plug end of the reservoir. Spacing of the protective membrane from the plug may be in the range of about 0.5 mm to 5 mm.

The plug comprises a polymeric matrix having an inorganic component and a stimulus-responsive component adapted to alter the porosity of the plug in response to a stimulus, such as an increase in glucose concentration, and thereby provide regulated release of insulin.

The stimulus-responsive component comprises a composite of at least one hydrogel that shrinks or swells (resulting in increased porosity or decreased porosity, respectively) when exposed to a stimulus, such as an increase in glucose concentration, and at least one second polymer or polymer mixture that does not change (e.g. does not shrink or swell) when exposed to the same stimulus. Examples of suitable hydrogels include poly(ethylene oxide), polymers of R-acrylamide, R-acrylate and $R_1$-acrylic acid, $R,R_1,R_2$-polysaccharides, or $R,R_1,R_2$-cellulose in which R, $R_1$ and $R_2$ may be H or alkyl (e.g. $C_1$-$C_{18}$) or —COOH containing groups. Examples of a suitable second polymer include crosslinked proteins and derivatives, e.g., bovine serum albumin, ethylcellulose, methylcellulose, propylcellulose, methoxypropylcellulose, hydroxypropylmethylcellulose, cellulose acetate, cellulose nitrate, poly(vinyl alcohol), poly(vinyl chloride), polystyrene, polyethylene, polypropylene, poly(ethylene-co-vinyl acetate), polyesters, e.g., poly(hydroxybutyric acid), poly(hydroxyvalerianic acid-co-hydroxybutyric acid), poly(lactic acid), poly(glycolic acid), poly(lactic acid-co-glycolic acid), poly(ϵ-caprolactones), poly(ϵ□-caprolactone-co-DL-lactic acid), polyanhydrides, e.g. poly(maleic anhydride), polyamides, albumin, gelatin, chitosan, collagen, pol(hydroxyalkyl)-L-glutamines, poly(γ-ethyl-L-glutaminate-co-glutamic acid), poly(L-leucine-co-L-aspartic acid), poly(proline-co-glutamic acid), poly(orthoesters), e.g. poly(alkyl 2-cyanoacrylates), polylysine, alginate, alginic acid, polyurethanes, poly(methyl methacrylate), poly(methyl methacrylate-co-methacrylic acid), and poly(methacrylate-co-hydroxypropyl methacrylate). The amount of hydrogel is about 20-40% w/w, preferably, about 30-35% w/w, and the amount of second polymer is about 20-70% w/w, preferably, about 40-50% w/w, both within the stimulus-responsive component.

Figure 2A:
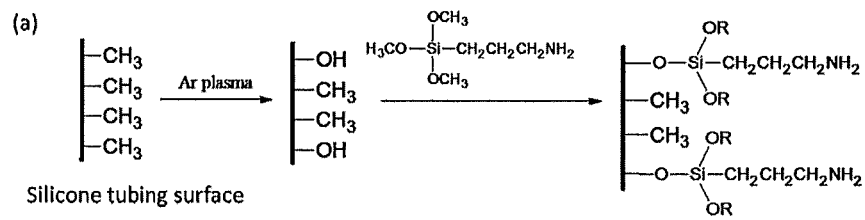
FIG. 2 is a schematic showing the reactions and steps involved in the surface modification of the device, including the silanization of the silicone tubing (A), crosslinking of the BSA-based plug with the amine groups of the silanized silicone tubing (B), the PEGylation of the device surface (C)
Figure 2B:
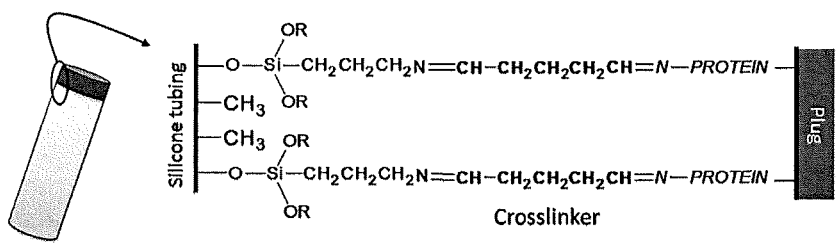

In addition, the stimulus-responsive component includes a catalytic component. The catalytic component is sufficient to catalyze the change (e.g. the shrinking or increase porosity) in the hydrogel in response to a hyperglycemic level of glucose, without any significant adverse effect on the biocompatibility of the device, that permits release of insulin from the device as shown in FIG. 2B. In one embodiment, the catalytic component comprises enzymes which catalyze the change in the hydrogel. For example, a glucose oxidase (along with any required cofactor, e.g. a flavin adenine dinucleotide (FAD) moiety) may be incorporated into the polymer matrix of the plug, to oxidize glucose, when present in hyperglycemic concentrations, which subsequently forms gluconic acid and hydrogen peroxide. The formation of gluconic acid in the presence of hyperglycemic concentrations of glucose results in a drop in pH sufficient to cause the hydrogel to shrink. Shrinkage of the hydrogel results in an increase in porosity and permits a flow of insulin from the reservoir of the device. Another enzyme, e.g. catalase, may form part of the catalytic component to break down the harmful hydrogen peroxide and regenerate oxygen that is needed for glucose oxidation. The amounts of the glucose oxidase and catalase in the glucose-responsive component may each be in the range of about 0.01% to 20% (w/w).

The inorganic component includes inorganic particles suitable at least to stabilize the structure of matrix forming the membrane or plug, and which may additionally increase the mechanical strength of the matrix forming the membrane or plug, enhance the activity and stability of the catalytic component, and may result in an increased recovery of oxygen from hydrogen peroxide as well as dampen the pH decrease at normal glucose levels, and/or may facilitate quenching of hydrogen peroxide. Examples of such inorganic particles include, but are not limited to, metals and their oxides, e.g. $MnO_2$, Mn, Ag, Au, $SiO_2$, titanium, iron, magnesium, silica-based materials, and non-hydrocarbon-based nanomaterials such as carbon nanotubes. The inorganic particles have particle sizes ranging from about 1 nanometer to about 1-10 millimeters. The inorganic particles are generally added to the composite in an amount in the range of about 0.01%-25% (w/w), for example, 1-25% (w.w), preferably 1-20% (w/w). The weight ratio of inorganic component: glucose oxidase: catalase may vary from about 0.1:0.1:1 to about 10:10:1. The inorganic particles may be coated by another inorganic material (e.g. such as metals and their oxides), organic material, or a polymer (e.g. polyelectrolytes, albumin) to improve their stability and biocompatibility.

The device regulates the rate of insulin release in response to glucose concentration. When glucose levels are normal (e.g. around 100 mg/dL), the production of gluconic acid is largely compensated by the medium buffering, the diffusion of gluconic acid, and the action of the inorganic component. As a result, the pH inside the membrane is close to the pH of the medium (i.e. pH of at least about 7.0). At this pH, the hydrogel component is in a swollen state, the membrane has low porosity and thus insulin release is slow. On the other hand, in the presence of hyperglycemic glucose levels (200-400 mg/dL), greater glucose oxidation results in a drop in pH that triggers the hydrogel component of the device membrane to shrink and increase porosity in the membrane, thereby resulting in insulin release. On release of insulin, the glucose levels return to normal within a period of time, resulting in a decrease in production of gluconic acid, a rise in local pH and subsequent expanding of the stimulus-responsive hydrogel component to prevent further insulin release. The glucose-regulated insulin release profile of the device is, thus, based on the reversible pH-sensitivity of the hydrogel component in the membrane or plug.

A method of preparing a glucose-responsive membrane/plug is also provided in another aspect of the invention. The method includes the steps of combining the inorganic component, at least one polymer that does not change dimension when exposed to a stimulus (e.g. increase in glucose concentration) and the catalytic component(s), adding at least one hydrogel that changes dimension when exposed to a stimulus to form a mixture, and then incubating the mixture with a cross-linking agent (e.g. such as glutaraldehyde or genipin) under conditions suitable to permit cross-linking and formation of the membrane. As one of skill in the art will appreciate, the cross-linking agent will be added in an amount suitable to render a membrane/plug in which the cross-linking density is appropriate to permit porosity changes in the membrane and to allow insulin release in response to a stimulus.

The reservoir, formed from a biocompatible material as described, may be prepared for attachment to the glucose-responsive plug. Functionalization of the surface of the reservoir may facilitate firm attachment of the plug or membrane to the reservoir. For example, silanization to introduce groups (e.g. amino groups) suitable for crosslinking with reactive groups on the surface of the plug or membrane may facilitate such attachment. The attachment of the plug or membrane to the reservoir may be achieved after the plug or membrane is formed or simultaneously with the formation of the plug or membrane. If the reservoir is open-ended, then it may be sealed as described above with appropriate materials. Finally, the device, including reservoir and plug, may be surface modified to optimize biocompatibility, for example, by PEGylation in a manner known in the art.

The present insulin delivery device is shaped to be suitable for implantation into a mammal to be treated. Thus, the device may be formed into various shapes and structures including cylindrical, spherical, disk-shaped or sheet-like. Generally, the dimensions of the device are no more than about 10 cm long, and preferably no more than about 5 cm long, and no more than about 5 cm wide. The size of the device will determine the volume of insulin that may be contained in the device. As one of skill in the art will appreciate, a smooth outer surface will facilitate implantation and use of the device.

Prior to implantation into a mammal, the device is filled with an insulin formulation, by injection, insertion or other suitable means, which may be in the form of a liquid, semi-solid or solid at body temperature. The insulin may be dissolved in a solution, dispersed in a suspension or paste, or dispersed within a solid matrix of a polymer, lipid, or an inorganic material. Such dispersed insulin particles generally dissolve gradually by liquid that penetrates the solid matrix and can be released through the glucose-responsive membrane or plug when the membrane is triggered to increase porosity. Further, as one of skill in the art will appreciate, insulin may be present in the formulation as a monomer, dimer or hexamer. Metal ions, e.g. $Zn^{2+}$, $Mn^{2+}$, $Cu^{2+}$, $Ca^{2+}$ or $Co^{2+}$, may be added to the insulin formulation in a range of about 0.01-0.25 mg/units to modulate the assembly and stability of insulin. In the liquid form, insulin may be dissolved in slightly acidified or neutral buffers, e.g. in normal saline solution, citrate, acetate, phosphate, Tris-HCl, Glycine-HCl, HEPES, HEPPS, or in a combination of two or more buffers. Non-ionic surfactants or water soluble polymers, such as sodium dodecyl sulfate, Pluronics®, dodecyl maltoside, glucopyranosides, sorbitans, polysorbates, poly(ethylene glycol), albumin, polyvinyl alcohol, polysaccharides, cellulose derivatives, block copolymers, or a combination thereof, may be added to the preparation to improve insulin stability and solubility. Insulin particles may be prepared by free-drying in the presence of sugar, surfactant or polymers that stabilize the insulin. The insulin particles may also be encapsulated in a gel using polymers and hydrogels, e.g. albumin, collagen, alginate, chitosan, polyacrylamide, gelation, arabic gum, starch and the like. In the solid or semi-solid formulations, the insulin particles may be dispersed in powders, in nano- or microparticulate form, with or without polymers, surfactants or any other stabilizer or dispersing material. Solid preparations may be compacted into different shapes, e.g. pallets, disks, sticks, rods and the like.

The insulin delivery device is useful in a method of treating Type 1 and Type 2 diabetes in mammals, including human and non-human mammals (animals). In this regard, one or more devices according to the invention may be implanted into a mammal in need of treatment for diabetes, either subcutaneously or intraperitoneally. Multiple devices may be implanted at different locations in the mammal, or at the same location in various arrangements, e.g. side-by-side, stacked, or bound by a mesh, glue or screws. As used herein, the terms "implant" or "implantation" are used to refer to the insertion or grafting of the insulin delivery device, either wholly or partially, into tissues, under the skin, or a body cavity. Implantation may be achieved using well-established techniques in the art.

Once implanted, the device functions to deliver insulin at a elevated rate in hyperglycemic conditions and may also provide basal release of insulin under normal glycemic conditions. As one of skill in the art will appreciate, replacement frequency of the device will vary on a number of factors, including but not limited to, the specifications of the device, number of refills and the insulin requirements of the mammal into which the device is implanted.

The release profile of the device may be delayed on implantation by coating the insulin-releasing membrane with a layer of biodegradable material, e.g. poly(lactide-co-glycolide), polyesters, polyanhydrides, gelatin or collagen. This is particularly useful when multiple devices are implanted into a single mammal. A first device may be uncoated and have an undelayed release profile, while the additional devices may be coated with varying amounts of biodegradable material to result in staged release of insulin by each device, one after the other. In this way, the frequency of replacing an empty implanted device with an insulin-filled device, or refilling of the device with a fresh insulin formulation, is reduced thus decreasing the stress on the mammal being treated with the implants.

Broadly stated, the present invention relates to a closed-loop glucose sensitive insulin delivery system that mimics the pancreatic function of blood glucose homeostasis with the design and fabrication of a prototype implantable device. The device is ideal for treatment of diabetes as it overcomes the limitations of insulin injection therapy and provides a means to better manage the disease.

Embodiments of the invention are described by reference to the following specific examples which are not to be construed as limiting.

Example 1

Synthesis of Hydrogel Nanoparticles

Poly(N-Isopropylacrylamide-co-methacrylic acid) (poly (NIPAM/MAA)) nanoparticles were synthesized by an aqueous dispersion polymerization process. NIPAM, MAA and N,N'-Methylene-bis-acrylamide (BIS), at a mole ratio of 1:1:0.068 were dissolved in DDI water giving a total concentration of 135 mM. Sodium dodecyl sulphate (SDS) at a concentration of 0.4 mM was added to stabilize the nanoparticles produced. The mixture was purged with $N_2$ and then potassium persulfate (2.1 mM) was added to initiate the polymerization. The reaction was carried out at 70° C. under $N_2$ atmosphere and stirring at 200 rpm for 4 h. The obtained nanoparticles were purified by membrane dialysis (molecular weight cutoff 12,000 to 14,000, Fisher Scientific) against DDI water. The diameter of the hydrogel nanoparticles was determined to be about 380±110 nm in pH PBS solution pH 7.4 (0.01M phosphate; 0.15M NaCl); 157±50 nm in PBS solution pH 5.0 (0.01M phosphate; 0.15M NaCl) and 325±109 when the pH was increased to 7.4 again. The size distribution was determined by dynamic laser light scattering.

Example 2

Synthesis and Characterization of $MnO_2$ Nanoparticles

The sonochemical reduction of permanganate with manganese ions was used to prepare $MnO_2$ nanoparticles (NPs). In brief, a potassium permanganate aqueous solution (5 mL, 0.05 mM) was kept under ultrasonic field for 30 s by using an ultrasonic processor probe operating at approximately 50 Hz (Heischer UP100H, Germany). Manganese acetate aqueous solution (1 mL, 0.07 mM) was added and the dark brown dispersion obtained was sonicated for an additional 30 s. Solid nanoparticles were isolated by ultracentrifugation, thoroughly washed with DDI water, and freeze-dried overnight. Prior to use, powdered $MnO_2$ NPs were redispersed in DDI water or PBS solution (20-30 mg·mL$^{-1}$) by ultrasonication (1 min/50 HZ) followed by stirring overnight.

Figure 3:
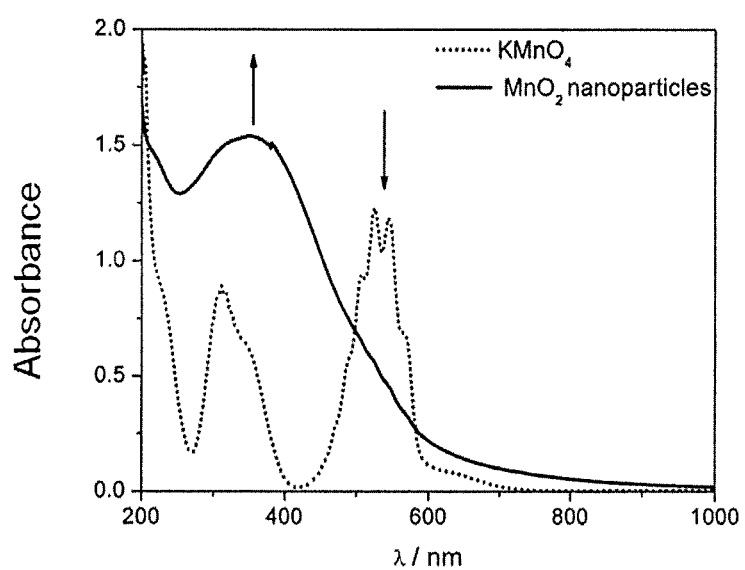
FIG. 3 shows UV spectra of reactant $KMnO_4$ and prepared $MnO_2$ nanoparticles.

Characterization of $MnO_2$ NPs was initially carried out from absorbance studies. The UV-Vis spectrum of the golden brown colloidal dispersion obtained is shown in FIG. 3. After the reaction with manganese acetate the three peaks centered at 315 nm, 525 nm and 525 nm originated from $KMnO_4$ disappeared and new broad peak at 360 nm, a characteristic of colloidal $MnO_2$ was observed, indicating the formation of $MnO_2$ NPs. TEM images of the $MnO_2$ nanoparticles revealed small discrete nanoflakes with an average size of about 80 nm.

Example 3

Preparation and Characterization of Glucose-Responsive Membranes

Membranes were prepared by crosslinking BSA with glutaraldehyde in the presence of 30 wt. % poly(NIPAM/MAA) NPs and various amounts of enzymes and $MnO_2$ NPs as follows:
(i) membrane 1: 5 wt. % GOx; (ii) membrane 2: 5 wt. % GOx and 10 wt. % $MnO_2$ NPs
(iii) membrane 3: 5 wt. % GOx and 1.6 wt. % CAT (CAT/GOx=0.29 w/w) and (iv) membrane 4: 5 wt. % GOx, 1.6 wt. % CAT and 10 wt. % $MnO_2$ NPs. In a typical preparation, to a small vial containing 6 mg of powder $MnO_2$ NPs dispersed in 200 µL of pH 5.0 PBS solution, 28 mg of BSA, 3 mg of GOx and 0.86 mg of CAT were introduced and incubated at 37° C. for 10 min. Following the addition of 85 µL of a 200 mg·mL$^{-1}$ dispersion of poly(NIPAM/MAA) NPs in DDI water, the mixture was stirred for 10 min, and then 15 µL of glutaraldehyde (grade I, 25%) was introduced. The mixture was quickly spread on a glass slide (~3.5×2.0 cm) and allowed to cross-link at room temperature for 1 h. The obtained membrane with approximately 400 µm in thickness was rinsed with DDI water, soaked in pH 7.4 PBS solution and kept at 4° C.

Determination of Mechanical Properties of Membranes

The stress-strain curves of wet membranes were measured using an Instron 3366 (USA). As-prepared membranes with dimensions of 50×25×0.8 mm were soaked in pH 7.4 PBS 24 h before measurements. Tests were carried out at 20° C. and ca. 50% relative humidity with a tensile speed of 0.5 mm/min and initial gauge length at 20 mm. The Young's modulus of elasticity was determined from the slope of the linear portion of the curves.

TEM, ESEM and SEM Measurements

Transmission electron microscopy (TEM) images of $MnO_2$ NPs were performed on a Hitachi H7000 microscope (Japan) at 75 kV. The $MnO_2$ colloidal dispersion was dropped on a charged copper grid. Environmental scanning electron micrographs (ESEM) were obtained in a Hitachi S3400 microscope (Japan) at 15 kV. As-prepared wet membranes were mechanically fractured, directly fixed onto a cold stage sample holder with double-sided carbon tape and frozen at −24° C. under 90 Pa. SEM images were obtained in a Hitachi S-3400N microscope (Japan) at 5-10 kV. Membrane samples were fractured in liquid nitrogen and dried at the critical point with liquid $CO_2$ in an Autosamdri—810 apparatus (Tousimis Research Corporation, USA). Samples were directly fixed onto the sample holder with double-sided carbon tape and coated with gold.

Figure 6:
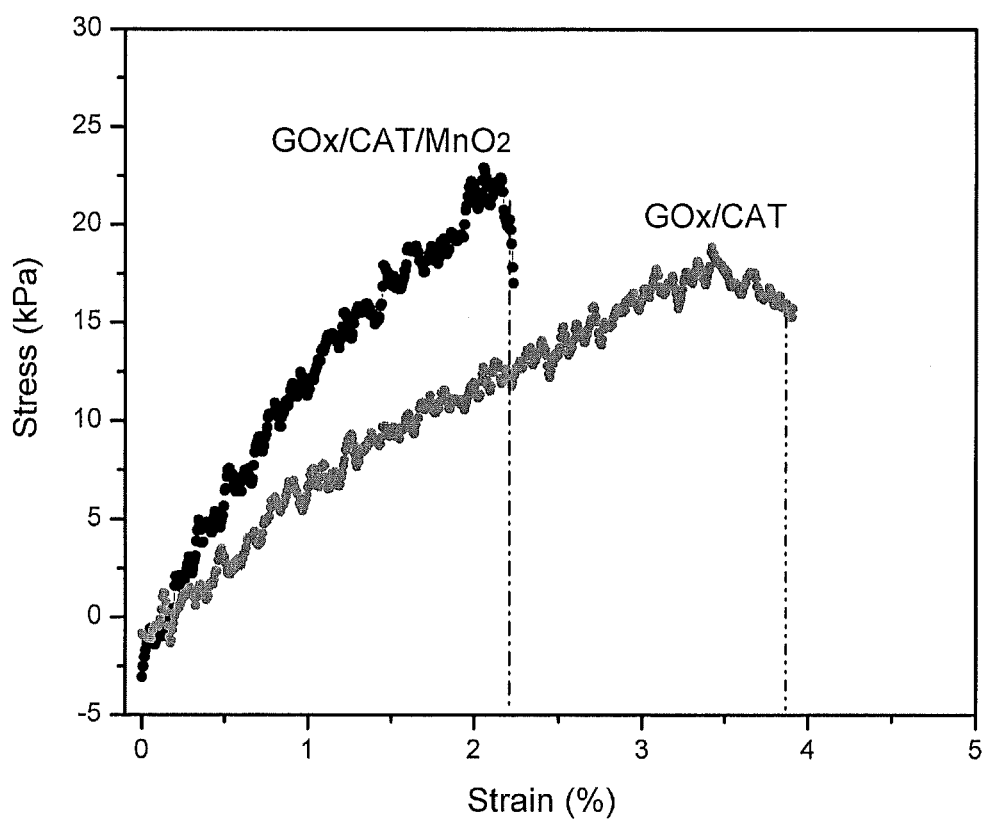
FIG. 6 graphically compares stress-strain curves of membranes with or without incorporated $MnO_2$ nanoparticles.

The mechanical strength and rigidity of the membrane is increased significantly due to the interaction of $MnO_2$ nanoparticles with the protein (FIG. 6). This interaction also resulted in more uniformly distributed rigid pores which allow the pH-sensitive nanoparticles to swell or shrink freely in response to changes in glucose concentration.

Example 4

Determination of Activity and Stability of the Immobilized GOx

The activity of immobilized GOx for oxidation of glucose was determined by using a glucose assay kit (HK—Sigma) in the presence of $MnO_2$ nanoparticles or CAT. At determined times, 10 µL of the medium was taken and added to 100 µL of assay kit, incubated for 15 min at room temperature and assayed using a microplate reader (Molecular Device, USA) at 340 nm. The amount of $H_2O_2$ produced by GOx-immobilized membranes or the amount of $H_2O_2$ quenched by CAT, $MnO_2$ nanoparticles or CAT with $MnO_2$ nanoparticles was measured by using PeroXOquant™ assay kit (Pierce, USA). Individual membranes (10×10×1 mm) were prepared containing a fixed amount of GOx=1 mg. Samples were soaked in 20 mL of 200 mg·dL$^{-1}$ glucose solution in pH 7.4 PBS solution and incubated at 37° C. At predetermined times, 10 µL of the medium was taken and added to 100 µL of assay kit, incubated for 15 min at room temperature and assayed using a microplate reader at 595 nm. Both assay kits were used according to the manufacturer's instructions.

Figure 4A:
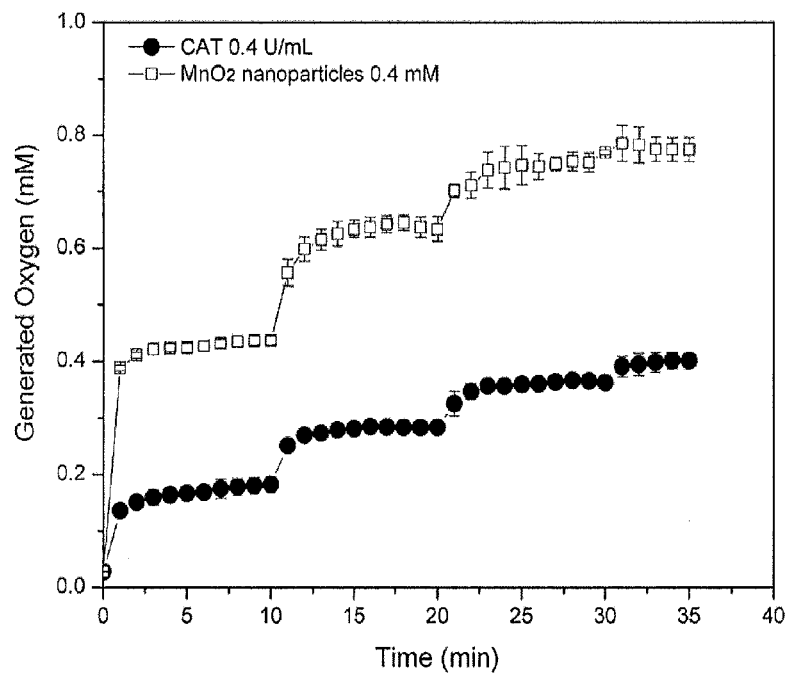
FIG. 4 graphically illustrates the effects of $MnO_2$ nanoparticles and catalase (CAT) on oxygen production (dissolved oxygen) from decomposition of $H_2O_2$ (A), and $H_2O_2$ generation in the presence of composite membranes containing immobilized GOx/CAT or GOx-CAT/$MnO_2$ nanoparticles (B)
Figure 4B:
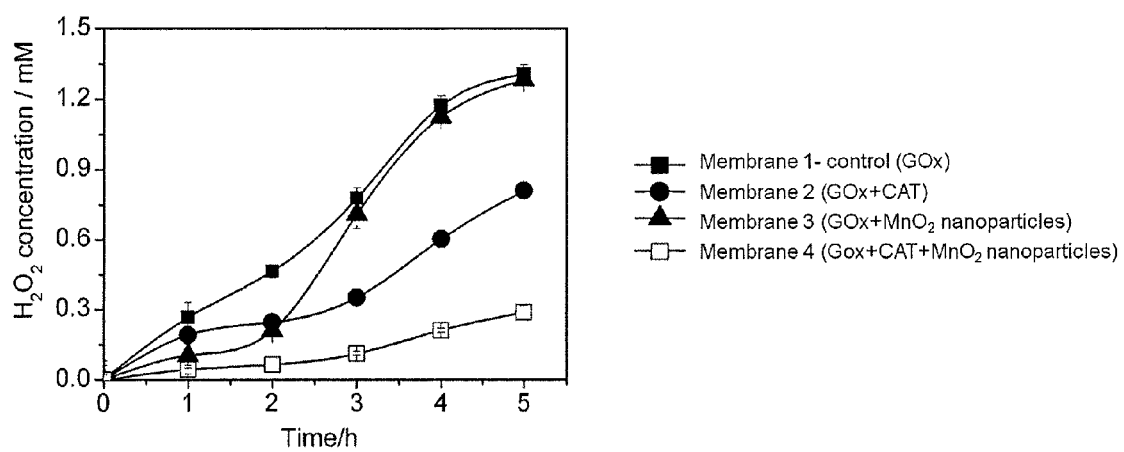

FIG. 4A shows that oxygen generation is increased in the presence of $MnO_2$ nanoparticles in comparison to the CAT alone. In addition, membranes incorporating CAT with $MnO_2$ nanoparticles exhibited greater $H_2O_2$ quenching activity than membranes with either alone (FIG. 4B).

Figure 5:
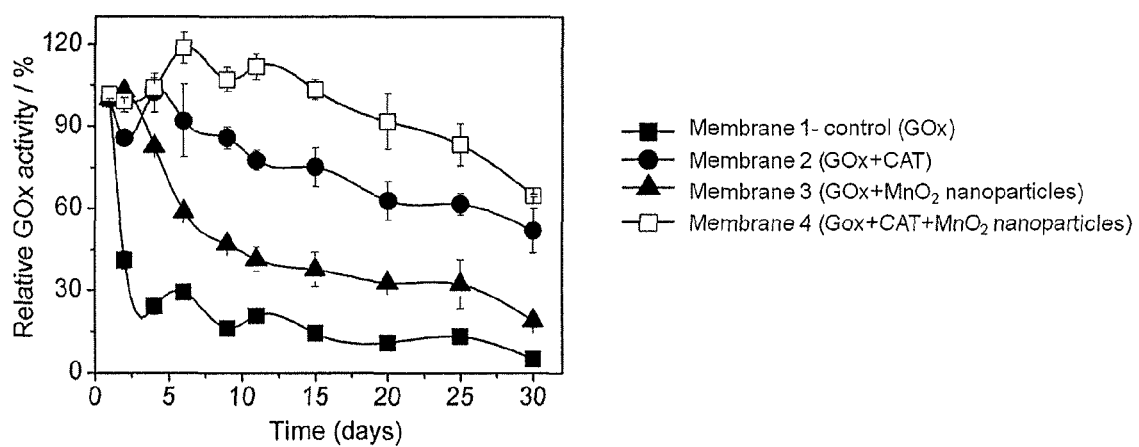
FIG. 5 graphically illustrates the relative activity of GOx in a membrane containing CAT, $MnO_2$ nanoparticles or CAT with $MnO_2$ nanoparticles.

The pH decrease of a glucose solution, another measure of GOx enzymatic activity and its relative stability during storage, was also determined by checking the ability of GOx to lower the pH of a glucose solution. Membranes with a dimension of 10×10×1 mm, each containing a 1 mg of GOx, were soaked in 5 mL of 200 mg·dL$^{-1}$ glucose solution in normal saline (NaCl 0.15M with pH adjusted to 7.4). Freshly prepared samples or samples stored in pH 7.4 PBS solution at 4° C. for various time periods up to 30 days were incubated at 37° C. and the pH of the solution was measured as a function of time. The slopes of the linear portion of the curves were calculated. The relative activity (RA) of immobilized GOx was calculated according the following equation:

$$RA\ (\%) = \frac{St \times 100}{St1}$$

where St1 and St are respectively the slope of the pH changes curve at time day 1 and at time day t. The results are illustrated in FIG. 5 showing that membranes incorporating CAT with $MnO_2$ nanoparticles exhibited greater relative GOx activity than membranes with either alone.

Example 5

Insulin Permeation Across Glucose-Responsive Membranes

The permeation of insulin through the membranes in response to glucose concentration was carried out using a horizontal side-by-side diffusion cell system (PermeGear, Inc., USA) at controlled temperature (37° C.). The receptor cell was filled with pH 7.4 PBS solution containing 0.02 mM of Pluronic F-68 and 100 mg·dL$^{-1}$ of glucose and the donor cell was filled with 1 mg·mL$^{-1}$ bovine insulin solution in the same medium. The initial glucose concentration in all experiments was 100 mg·dL$^{-1}$. Aliquots of highly concentrated glucose solution (20 g·dL$^{-1}$) were then added to increase the glucose concentration to 200 and/or 400 mg·dL$^{-1}$ after a predetermined time. The solution in the receptor cell was continually pumped to a UV-flow cell and the insulin permeation was determined by measuring insulin absorbance at $\lambda$=276 nm using an UV spectrophotometer (HP 8453 UV Spectrophotometer, USA). The slope of the curves was calculated and the permeability of insulin (P) (cm$^2$·s$^{-1}$) was calculated according the following equation:

$$P = \frac{\text{slope of the Permeated Insulin curve (mg·}s^{-1}\text{)} \times \text{membrane thickness (cm)}}{\text{Insulin concentration in the donor cell (mg·cm}^{-3}\text{)} \times \text{area of permeation (cm}^2\text{)}}$$

The glucose-responsiveness of membrane permeability was defined as the ratio of insulin permeability measured at glucose=200 and 400 mg·dL$^{-1}$, to that at 100 or 200 mg·dL$^{-1}$, i.e., $P_{200}/P_{100}$; $P_{400}/P_{200}$; $P_{400}/P_{100}$.

To determine the regulated profile of insulin release after each cycle the membrane was kept in the diffusion cell. Solutions in both cells were removed, the apparatus was rinsed with pH 7.4 PBS solution, and fresh solutions were added in the donor cell (Insulin 1 mg·mL$^{-1}$ in the medium) and the receptor cell (just medium). Glucose concentration was alternated every 2 h between 100 and 400 mg/dL$^{-1}$ in five consecutive cycles.

Figure 7A:
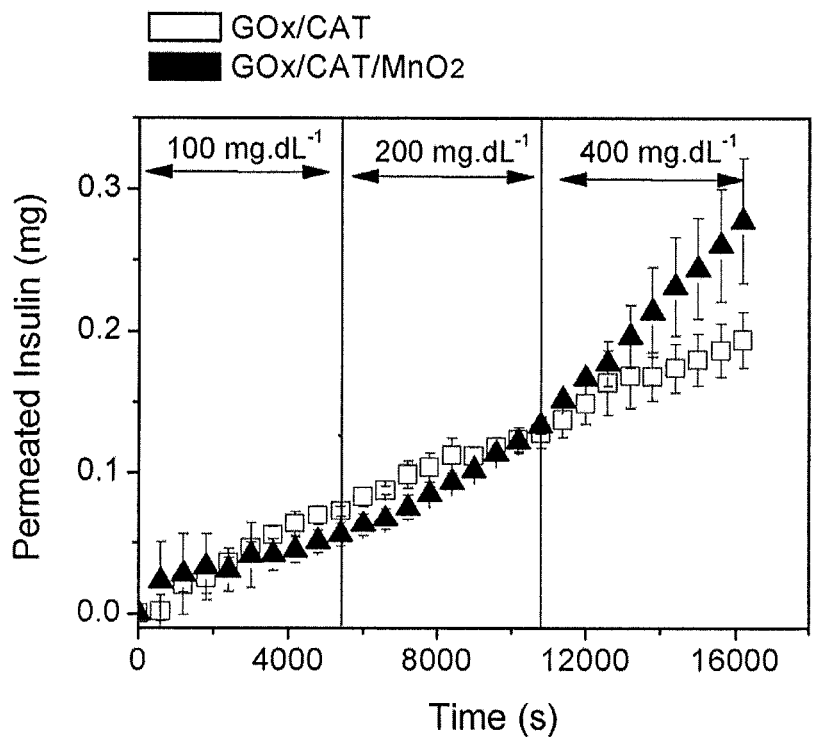
FIG. 7 graphically illustrates the profile of insulin permeation across membranes containing immobilized GOx/CAT or GOx/CAT/$MnO_2$ nanoparticles in response to step-wise change of glucose concentration (A), and insulin permeability as a function of glucose concentration (B)
Figure 7B:
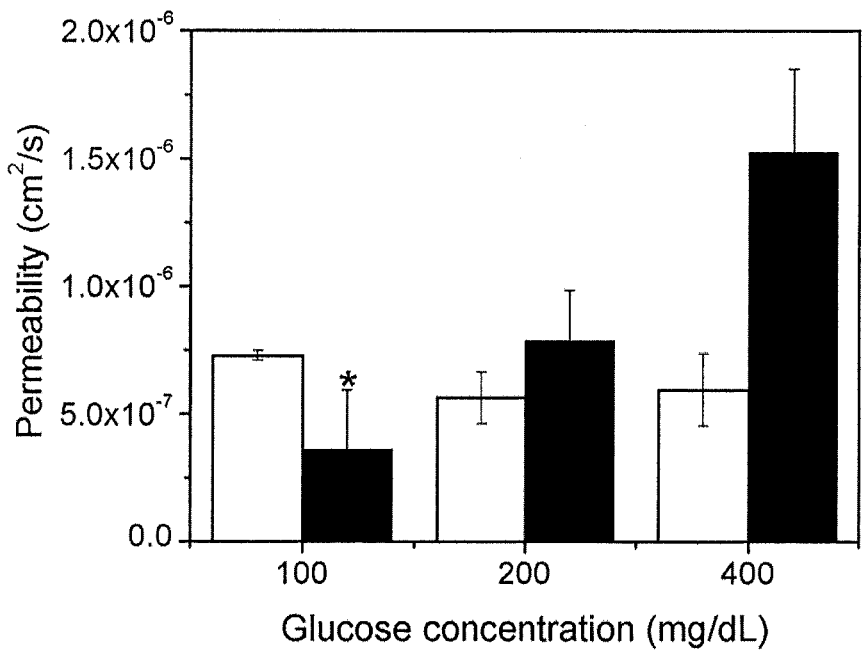

The glucose-responsive insulin release across the membranes is compared in FIG. 7. For the membrane containing $MnO_2$ nanoparticles, the rate of insulin permeation increases with increasing glucose concentration. The permeability of insulin, calculated from the slopes of the curves presented in FIG. 7a, is significantly higher at higher glucose concentrations at 200 mg/dL and 400 mg/dL than at 100 mg/dL for the membrane with $MnO_2$ nanoparticles, while the permeability of the membrane without $MnO_2$ nanoparticle remains steady (FIG. 7b). For the membrane containing $MnO_2$ nanoparticles, the permeability of insulin increases about two-fold when glucose is increased from 100 to 200 mg·dL$^{-1}$ and from 200 to 400 mg·dL$^{-1}$ ($P_{200}/P_{100}$ and $P_{400}/P_{200}$=2.18 and 1.95, respectively ($p<0.05$)), and about four-fold when the glucose concentration is increased from 100 to 400 mg·dL$^{-1}$ ($P_{400}/P_{100}$=4.23 ($p<0.05$)).

The superior mechanical and morphological properties imparted by $MnO_2$ nanoparticles led to glucose-dependent insulin release across the membrane.

Example 6

Preparation of an Insulin Delivery Device

The insulin delivery device was prepared in five steps as follows:

Step 1—Surface Modification of Silicone Tubing:

Silicone tubing (length=3 cm) was oxidized for 20 min in a 5 W air plasma and then immersed in 0.1M 3-aminopropyltrimethoxysilane in anhydrous ethanol overnight. Silanized tubing was extensively rinsed with ethanol and blow-dried with nitrogen gas at room temperature. In this process the surface hydroxyl groups, generated by oxidation with air plasma, were reacted with a trialkoxysilane derivative. The condensation between grafting molecules and surface groups generate highly stable Si—O—Si bonds creating a functional self-assembled monolayer on the surface, which can consist of aminopropyl or any other silane derivative (FIG. 2A). The chemical composition of silicone tubing before and after silanization, as determined by X-ray photoelectron spectroscopy (XPS) reflects a clear alteration in the surface chemical composition after the silanization. In the XPS analysis, a strong N1s signal was observed for the silanized tubing (% N=1.13). This signal was not visible on the blank silicone (% N=0.00), indicating that the aminopropyl groups are successfully coupled to the tubing surface in an order of magnitude comparable with the depth of information of XPS, i.e. 5-10 nm. The silanization step increases the hydrophilicity of the tubing surfaces to prevent insulin aggregation in the reservoir. Also, the functionalization with amine groups allows for the direct crosslink of the glucose-responsive plug with the tubing surfaces.

Step 2—Crosslinking of the Glucose-Responsive Plug with Silanized Silicone Tubing:

One end of the silanized tubing was sealed with a glucose-responsive plug as follows. In a small vial, powder inorganic nanoparticles (e.g. nano-$MnO_2$) (6 mg) were dispersed in pH 5.0 phosphate buffer (200 μL). Then, bovine serum albumin (28 mg), glucose oxidase (3 mg) and catalase (0.86 mg) were dissolved in the dispersion by incubating 10 min at 37° C. pH-responsive hydrogel nanoparticles were added (85 μL, 200 mg·mL$^{-1}$ dispersed in DDI water) and the mixture was stirred 10 min. Then, glutaraldehyde 25% (15 μL) was added and the mixture (2.5 μL) immediately transferred to one end of the tubing. The obtained plug was crosslinked at room temperature for 30 h, then rinsed with DDI water and soaked in pH 7.4 phosphate buffer overnight at 4° C. The glucose-responsive plug was prepared by the crosslink of proteins with glutaraldehyde in the presence of the pH-responsive hydrogel nanoparticles, inorganic nanoparticles and enzymes. The crosslink process occurs inside one end of the silanized silicone tubing leading to a plug at about 1 mm in thickness. Since amine groups were introduced on the tubing surface, the covalent coupling of the protein-based plug with the silanized tubing occurs as shown in FIG. 2B.

Step 3—Polymer Sealing:

The open end of the tubing was dipped in a polymer solution, (e.g. ethylene-vinyl acetate copolymer resin solution 8% in dichloromethane (w/v)) and immediately blow-dried with air for approximately 1 min. The procedure was repeated at least 10 times until a round coating was obtained.

Step 4—Coupling of PEG Derivative (PEGylation)

Figure 2C:
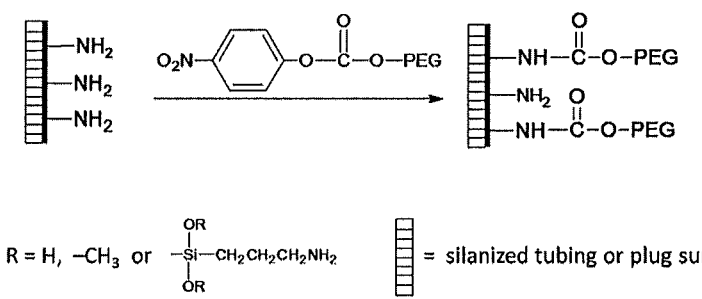

Devices were soaked in 0.01M of activated PEG (poly(ethylene glycol)) in pH 7.4 phosphate buffer for 48 h at 4° C. Devices were extensively washed with DDI water and kept in pH 7.4 PBS at 4.0 prior to use. Coupling of PEG was accomplished through the amide bond formation between COO of activated PEG and $NH_2$ of protein molecules present on plug surface (FIG. 2C). Since amine groups were introduced on tubing surface through the silanization process, the coupling of activated PEG with the aminopropyl groups on silicone surface also occurs. Characterization of the products by NMR shows the characteristic peak for PEG at 4.4 ppm suggesting that the PEGylation of the plug and silanized tubing is successfully achieved.

Step 5—Insulin Formulation

Insulin Stock Solution:

The device was filled with highly concentrated neutral buffered insulin solution. e.g. insulin (25 mg) and n-octyl-β-D-glucopyranoside (3.65 mg) were dissolved with 0.1M NaOH aqueous solution (600 μL). (4-(2-hydroxyethyl)-1-piperazineethanesulfonic acid (HEPES) was added (12.6 mg) and the volume brought to 1 mL by slowly adding 0.1M HCl aqueous solution. Devices were filled with this solution (≈50 μL, 1.25 mg insulin per device) by using a syringe with a thin needle. Air bubbles were avoided by piercing a second needle in the opposite side of the device.

Insulin Gel Formulation:

Insulin gel formulation was prepared using an in situ solubilization method. Human recombinant insulin and Pluronic F127 were dissolved in a glass vial with 0.1M NaOH solution to give a concentration of 100 mg/ml and 2.5 mg/ml, respectively. After both insulin and surfactant were dissolved completely, pH was adjusted to ~8 by dropwise addition of 5 μl 1M HCl, with slow agitation to redissolve precipitates between additions. Pluronic F127 was increased to 25% and 1% hydroxypropyl methylcellulose (HPMC) was added to increase viscosity. Insulin gel formulation was kept at 4° C. until both Pluronic F127 and HPMC dissolved. Devices were filled with this solution (≈50 μL, 5 mg insulin per device) by using a syringe with a thin needle Gelation was induced by incubation of the device at 37° C.

Microcrystalline Insulin:

Microcrystalline Insulin was prepared by a polythermal method. Powder human insulin (10 mg) was added to a 20-mL glass scintillation vial containing Pluronic F-68 or F-127 (0.003 g). Then, 0.02M HCl solution (2.5 mL) and 20 wt % $ZnCl_2$ solution (12 uL) were added to the vial and a clear insulin solution was obtained. Insulin was then precipitated at its isoelectric point by adding a 0.2 M sodium citrate solution (500 uL). The turbid solution was quickly heated to 50° C. in a water bath to afford a clear solution. Slow cooling of this solution to room temperature overnight afforded well-defined microcrystalline Zn-insulin. In a next step, crystals were allowed to set; the supernatant was carefully removed and the crystals were re-suspended at desired concentration (50-100 mg/mL) with a stabilizing solution containing $ZnCl_2$ 0.05 wt. % and methylparaben 0.1 wt. % with pH adjusted to 7.4. Crystals without Pluronic were prepared in a similar way except that pluronic was omitted.

Example 7

In Vitro Insulin Release from the Insulin Delivery Device

Figure 8A:
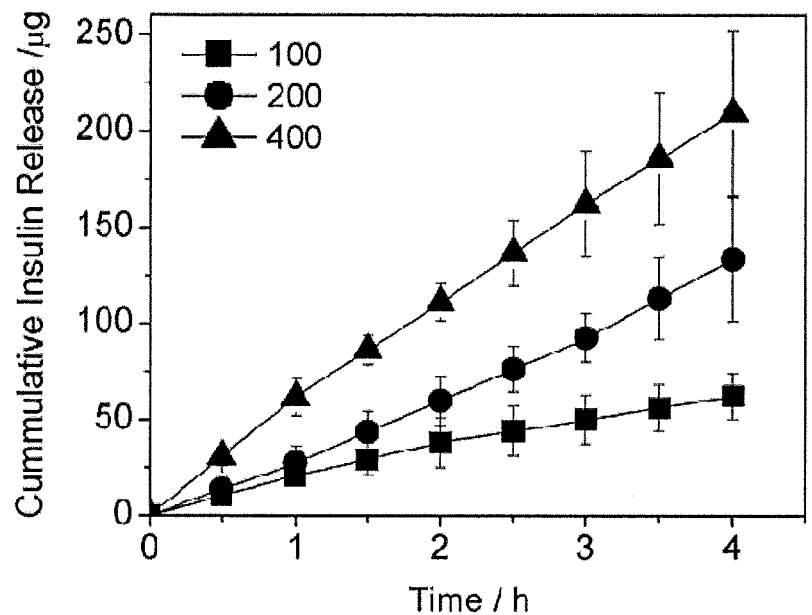
FIG. 8 graphically illustrates in vitro release of insulin from a device over time at glucose concentrations of 100, 200 and 400 mg·$dL^{-1}$ (A), the rate of insulin release ($\mu g·h^{-1}$) from the device as a function of glucose concentration (B) and an insulin release profile of the device as glucose concentration was alternated between 100 and 400 mg·$dL^{-1}$ in four cycles (C). Data points represent mean±SD (n=3-5)
Figure 8B:
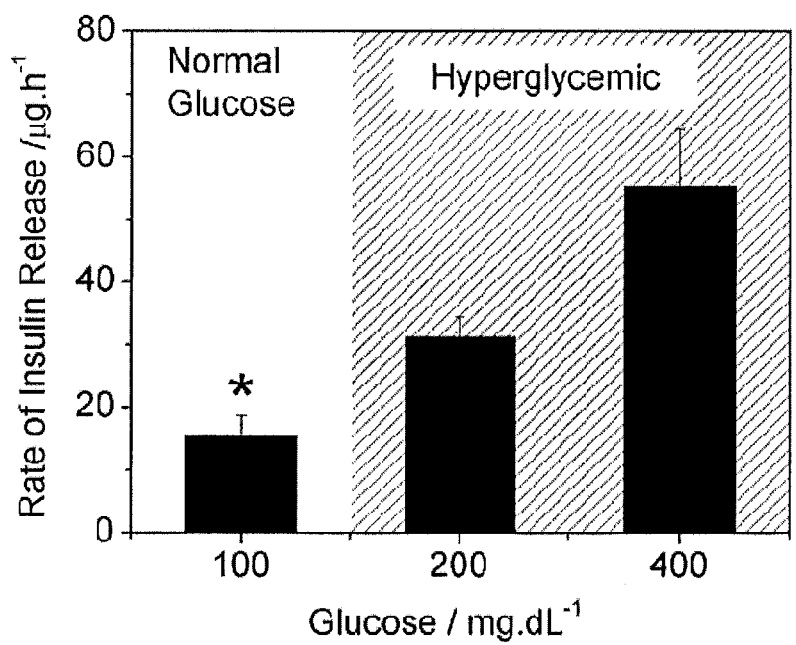
Figure 8C:
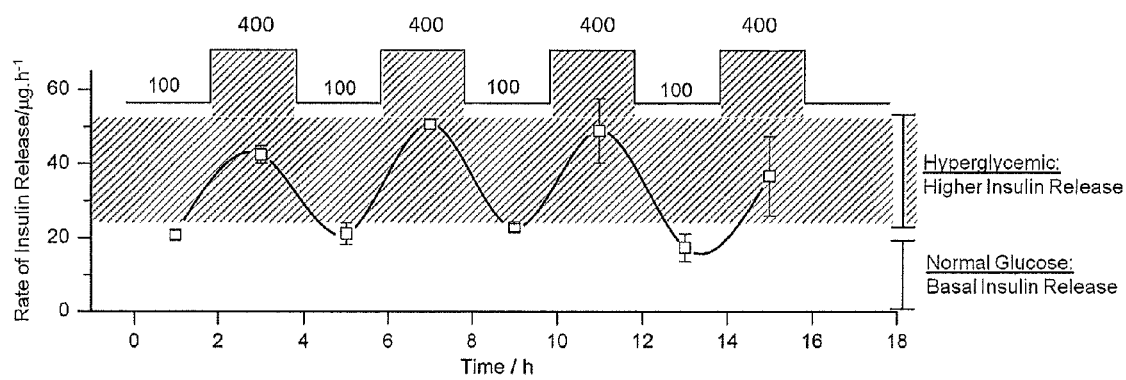

In vitro release of insulin was determined over time as a function of glucose concentration. Devices were individually placed in glass vials containing the release medium (3 mL of pH 7.4 phosphate buffer containing glucose 100 mg·$dL^{-1}$ and Pluronic® F-68 0.02 mM). Vials were sealed and kept under constant mixing in a hematology mixer. The release medium was replaced every 1 h and the insulin release was determined by measuring insulin absorbance manually in a UV/VIS spectrophotometry every 15 min at λ=276 nm. The rate of insulin release was determined by the slope of the curves. The experiment was repeated with the same devices using glucose concentrations=200 and 400 mg·$dL^{-1}$ in the release medium. For each set of experiments, the devices were refilled with fresh insulin solution in order to guarantee the same concentration of insulin in the devices in all experiments. The glucose-responsiveness of the insulin delivery device was defined as the ratio of the rate of insulin release (R) determined at hyperglycemic glucose (i.e., 400 mg·$dL^{-1}$), to that at normal glucose (100 mg·$dL^{-1}$), i.e., $R_{400}/R_{100}$. As observed from the plots (FIG. 8), a relative higher rate of insulin release was obtained at hyperglycemic glucose levels. The rate of insulin release increased about two-fold when glucose in the release medium was increased from 100 to 200 mg·$dL^{-1}$ and 200 to 400 mg·$dL^{-1}$ ($R_{200}/R_{100}$ and $R_{400}/R_{200}$=2.1 and 1.8, respectively ($p<0.05$)).

To check the regulated profile of insulin delivery device in response to alternated changes in glucose concentration, devices were individually placed in glass vials containing the release medium described above. Vials were sealed and kept under constant mixing in a hematology mixer. After 2 h the glucose concentration in the medium was increased to 400 mg·$dL^{-1}$. The same procedure was repeated for subsequent alternated cycles. As demonstrated (FIG. 8), the insulin release profile of the device exhibited a pulsatile pattern when glucose concentration was alternated between normal (100 mg·$dL^{-1}$) and hyperglycemic levels (400 mg·$dL^{-1}$) in several cycles. The device responded quickly to changes in glucose level in the release medium. A three-fold increase in the insulin release rate was observed when the glucose concentration was increased to a hyperglycemic level. Additionally, the insulin release rate decreased to the initial rate when the glucose concentration was decreased to the normal level, demonstrating the glucose-regulated profile of the insulin delivery device. Also, the plots clearly show that the device presents a basal insulin release rate (about 20 μg·$h^{-1}$) at normal glucose levels, what is highly desirable in insulin therapy.

The glucose-regulated insulin release profile of the device is based on the reversible pH-sensitivity of the bio-inorganic glucose-responsive. The plug consists of a porous bio-inorganic polymeric matrix embedded with pH-responsive hydrogel nanoparticles and the enzymes, glucose oxidase and catalase. In this system the porosity of the plug is increased at hyperglycemic glucose levels in response to enzymatic oxidation of glucose to gluconic acid, which leads to the shrinkage of the hydrogel nanoparticles, increased porosity of the plug and a higher insulin release rate.

Example 8

Biocompatibility of the Insulin Delivery Device

STZ (streptozotocin)-induced diabetic male Sprague Dawley rats were used for the in vivo experiments. To evaluate the biocompatibility of the device rats were randomized into 2 groups and implanted with silanized devices or PEGylated insulin delivery devices, both subcutaneously (SC) in the interscapular tissue and intraperitoneally (IP). After 5 days post-implantation, the animals were sacrificed and the devices were carefully explanted. Retrieved devices encapsulated with new-formed surrounding tissue were fixed in formalin 10%, embedded in paraffin and used for histological analysis.

The rats tolerated the devices very well as there were no signs of ongoing inflammation or insufficient wound healing at the sites of implantation. The biological response to the implanted devices was evaluated by histological analysis of the tissue surrounding the devices after 5 days implantation period. A significant difference between silanized and PEGylated devices was observed, either for IP or SC implantation. For the silanized device a very dense capsule is formed around the plug for devices implanted SC or IP. For the IP implantation a thick layer of inflammatory cells is observed in the device-tissue interface indicating an inflammatory reaction in response to the implanted device. A significant improvement in cellular response was found when PEG is introduced on the device surface. For devices with PEGylated surface a thin capsule or no capsule is observed for devices implanted SC or IP, respectively. The contrasting difference in encapsulation between PEGylated and silanized devices demonstrates a differential chronic tissue reaction in response to the surface chemistry of the device. These results indicate that the PEGylation of the device increases the biocompatibility by masking the device surface against immune cells response. Tissue encapsulation is dependent on the site of implantation and device surface chemistry.

Example 9

In Vivo Performance of the Insulin Delivery Device

The performance of the insulin delivery device was evaluated in vivo by assessment of glycemia in diabetic-induced rats. Male Sprague-Dawley rats (300 g-350 g) were exposed to a 12/12 reverse-light cycle, fed rat chow and water ad libitum. Rats were induced to become diabetic by intraperitoneal injection of streptozotocin (STZ; 65 mg·kg$^{-1}$ in sterile saline). Before implantation surgery, rats were cannulated under isofluorane anesthesia to allow for easy daily blood samples. After three days of recovery, rats were randomized into 2 groups. Group 1 was implanted with saline-filled device (n=5, Sham) and group 2 was implanted with insulin-filled device (n=5, ~6 mg insulin implanted per rat). Fed glucose levels were monitored on a daily basis using a glucometer. Blood was withdrawn from the catheters for plasma insulin level determination using an antibody radioimmunoassay kit specific for rat insulin. After an 8-day implantation period, animals were sacrificed and the devices retrieved for further experiments.

Figure 9A:
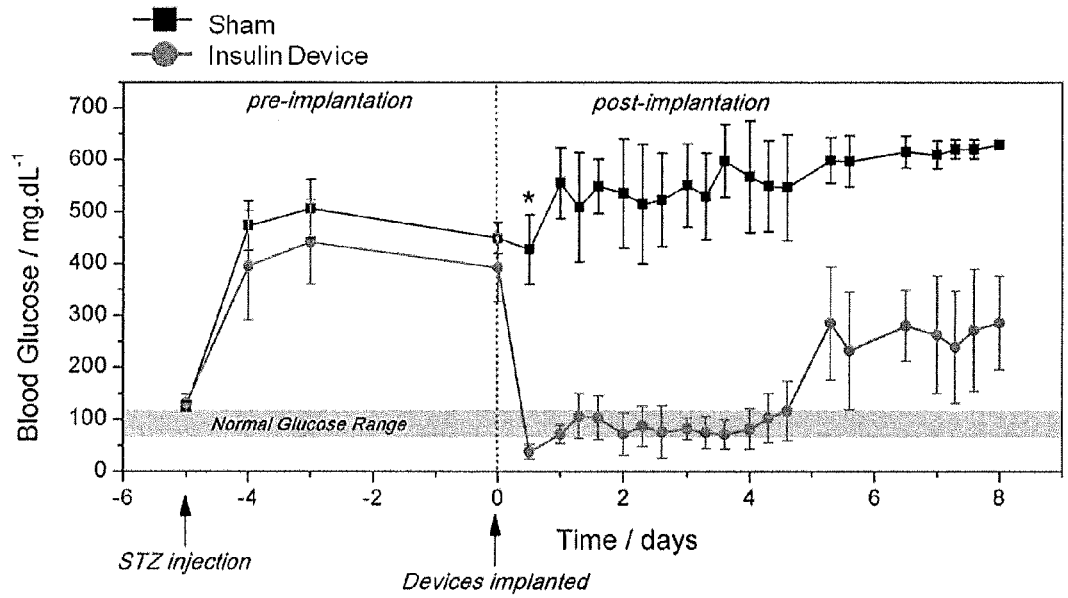
FIG. 9 graphically illustrates the effect of the device on the blood glucose levels (A) and insulin levels (B) in diabetic rats.
Figure 9B:
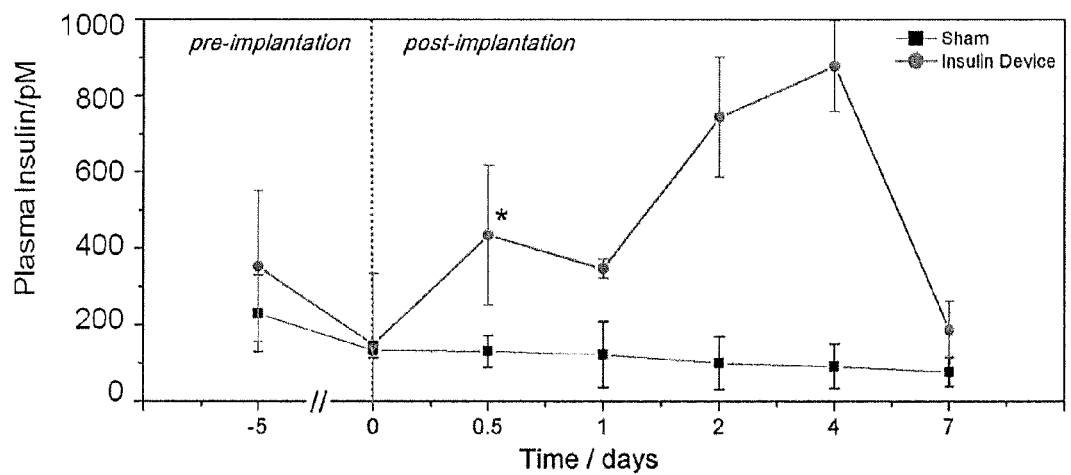

In the experiment, rats were induced to become diabetic by the injection of streptozotocin (STZ). STZ causes pancreatic β-cell destruction, resulting in a dramatic decrease in insulin levels. The diabetic state of the rats was confirmed with elevation in the blood glucose from 130 to >450 mg·dL$^{-1}$ (FIG. 9A). All rats were left untreated for 5 days to confirm the diabetic state prior to the intraperitoneal implantation of the device. The glucose levels and the plasma insulin levels of the rats were monitored on a daily basis during the 8-day implantation period. The device released insulin in vivo for up to 8 days. Rats implanted with insulin-filled device showed higher levels of plasma insulin than the sham group throughout the implantation period (FIG. 9B). The implantation of the insulin device caused a dramatic effect on the glycemic control of the diabetic rats compared to the sham. Upon implantation, animals in the insulin group showed an almost immediate drop of plasma glucose from hyperglycemic to hypoglycemic levels. However, this hypoglycemic effect seems to be mitigated over the course of the rest of the experiment and the blood glucose of the group was maintained in the normal level (~90 mg·dL$^{-1}$) for up to 6 days without peaks of hyper or hypoglycemic states (FIG. 9A). After 6-day implantation period, the blood glucose levels of the insulin group started increasing to hyperglycemic levels (~250 mg·dL$^{-1}$) but were still significantly lower than the sham (>600 mg·dL$^{-1}$). The increase in the blood glucose of the insulin group after 5-days implantation period was attributed to the decrease in the insulin content of the device (which could lead to lower insulin release rates) or due to loss of bioactivity of the encased insulin. It is also important to point out that, after 8-day implantation period, the group implanted with the insulin device gained weight and looked much healthier than the control group, evidencing the efficacy of the treatment with the insulin delivery device. A longer duration of effectiveness of the device containing higher insulin concentrations (i.e., 50 mg·mL$^{-1}$ and 100 mg·mL$^{-1}$ in a gel formulation) was obtained. Insulin release from the implanted device and suppression of glucose levels in diabetic rats lasted for 15 days.

Example 10

In Vivo Glucose-Challenge Test of the Insulin Delivery Device

Figure 10:
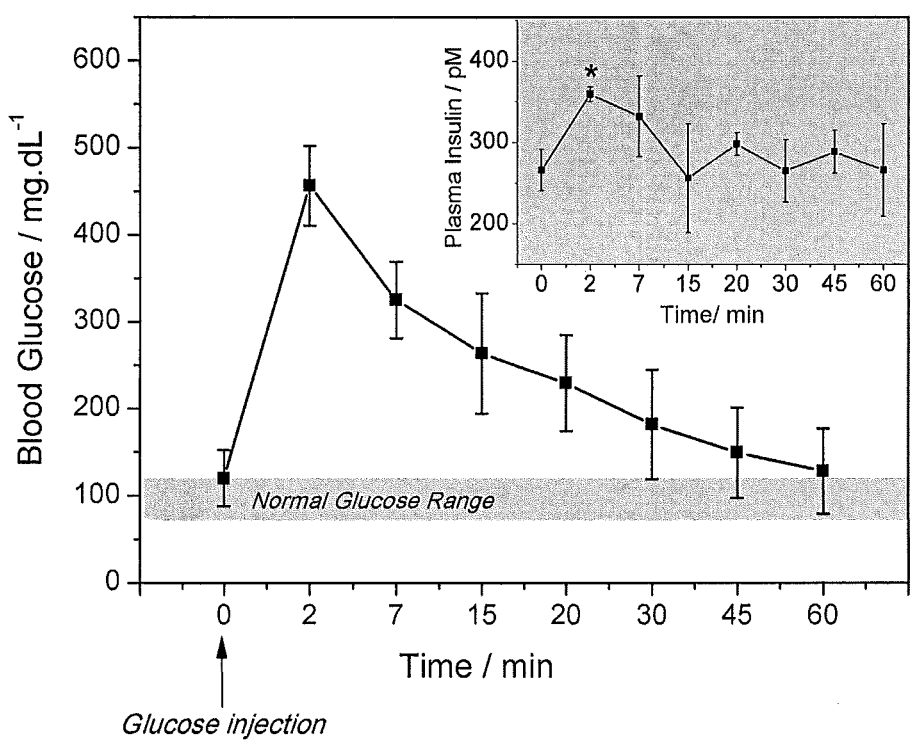
FIG. 10 is a graph showing the in vivo glucose-responsiveness of a device implanted in diabetic rats following a glucose challenge.

STZ-induced diabetic rats were implanted with insulin delivery device as described above and allowed for 24 h to confirm the decrease of blood glucose to normal levels by the action of the implanted devices. Rats were then challenged with intravenous injection of glucose (1 g·kg$^{-1}$, 50% dextrose), and their blood glucose was continuously monitored during 1 h. Upon the glucose injection the blood glucose level of the rat was increased from normal to hyperglycemic level; after less than 20 min the glucose was decreased to normal levels in response to the action of insulin delivered from the implanted device (FIG. 10). These results demonstrated the glucose-regulated profile of the device in vivo by challenging implanted rats with glucose.

Example 11

Effect of PEGylation on In Vivo Performance of the Insulin Delivery Device

Materials:

All chemicals were analytical grade and used without further purification. Bovine serum albumin (99%), catalase (solution 13 mg·mL$^{-1}$), 3-aminopropyltrimethoxysilane 97%, glutaraldehyde 25% (grade I), poly(ethylene glycol) methyl ether ($M_W$ 2 000 and 20 000), 4-nitrophenyl chloroformate (NPC) and tri-pentylamine (TPA) were purchased from Sigma-Aldrich. Glucose oxidase (230 U·mg$^{-1}$) was purchased from Calzyme (USA). Recombinant human insulin (r-DNA origin, 27 U·mg$^{-1}$) was purchased from Wisent (Canada). Pluronic® F-68 and F-127 were provided by BASF Corporation (Germany). HEPPS (4-(2-hydroxyethyl)-1-piperazinepropanesulfonic acid) was from MP Biomedicals (USA). Silicone tubing (Nalgene 50 silicone tubing, ID=1.6 mm, OD=3.2 mm, wall=0.8 mm) was purchased by Nalgene (USA). Ethylene-vinyl acetate copolymer resin (EVAC, ELVAX-40W) was provided by E. I. Du Pont. Poly(N-Isopropyl acrylamide-co-methacrylic acid) (NIPAM/MAA) nanoparticles (200±110 nm in pH 7.4 phosphate buffered saline (PBS) and 60±50 nm in pH 5.0 PBS, volume distribution) and powder nano-MnO$_2$ (80±30 nm) were prepared as previously described without further modifications. Distilled and deionized (DDI) water were obtained from a Milli-Q water purifier (Millipore Inc.). PBS pH 5.0 or pH 7.4 was prepared with 0.01 M phosphate and 0.15 M NaCl in DDI water.

Activation of 2 kDa and 20 kDa PEG:

mPEG was activated with NPC as described Jo et al., Biomacromolecules, 2001. 2: 255. Briefly, NPC and TPA were mixed in the molar ratio 1:5:5 (PEG:TPA:NPC). mPEG (2 g) was dissolved with toluene (20 mL) under nitrogen atmosphere. The temperature of the resulting solution was increased to 60° C. and 0.15 mL TPA was added followed by 100 mg NPC. After 24 hrs under stirring, the temperature was reduced to 35° C., 20 mL methyl-t-butyl ether was added and the solution was allowed to stir for 5 min. The reaction flask was then placed in an ice bath and the resulting thick slurry was stirred for another 30 min. The obtained solid was isolated by centrifugation (3000 rpm), dried under vacuum and re-dissolved with methanol (10 mL) at 40° C. The methanol solution was added dropwise in ice cold isopropanol (30 mL) under stirring, and the white solid obtained was collected by centrifugation (3000 rpm). The washing step was repeated two more times to remove unreacted molecules, and finally dried under vacuum for 24 hrs at room temperature. The activation of mPEG with NPC was confirmed by and verified using proton 400 MHz $^1$H NMR spectrometer (Varian Mercury 400, Varian Inc.).

Preparation of Microdevices:

Glucose-responsive bioinorganic microdevices were prepared as previously described. Briefly, medical grade silicone tubing (length=3 cm) was surface treated with oxygen plasma and silanized with 3-aminopropyl trimethoxysilane (0.1 M in ethanol). Silanized devices were crosslinked with a mixture of bovine serum albumin (51 wt. %) glucose oxidase (5.5 wt. %), catalase (1.56 wt. %), $MnO_2$ NPs (11 wt. %) and NIPAM/MAA NPs (30 wt. %) to create a bioinorganic membrane at one end of the tubing. Glutaraldehyde was used as a crosslinker (0.08:1 mol crosslinker to protein ratio). The other end of the tubing was sealed with EVAC solution (18% w/v in dichloromethane). Surface PEGylation of microdevices was achieved by soaking in 0.1M activated PEG solution (2K or 20K) in PBS pH 7.4 for 24 h. Microdevices were washed several times with DDI water. Buffered insulin solution (human insulin 50 mg·$mL^{-1}$, HEPPS 50 mM, Pluronic F68 0.02M, pH~8) was utilized to fill the devices prior in vitro and in vivo studies (≈50 μL, 2.5 mg or 67.5 units insulin per device). For this, a thin needle (27½ G) was utilized and air bubbles were prevented by piercing a second needle in the opposite side of the device during the filling step. Devices were stored in pH 7.4 PBS at 4° C. prior to use.

In Vitro Test of Glucose-Responsiveness of the Device:

Microdevices were placed in glass vials containing pH 7.4 PBS (2 mL) and glucose (100 mg·$dL^{-1}$) as release medium, and placed on rotary mixer at 37° C. for the duration of the experiment. Insulin release was determined by monitoring insulin absorbance manually with a UV/VIS spectrophotometer (Lambda 25 UV/VIS spectrometer, Perkin Elmer, USA) every 30 min at =276 nm. Glucose concentration was increased from normal (100 mg·$dL^{-1}$, 0-2 h) to hyperglycemic levels (400 mg·$dL^{-1}$, 2-4 h) halfway through the duration of the experiment.

Biocompatibility and In Vivo Stability of the Microdevice:

Microdevices were prepared with different surface treatments (no PEG, 2 kDa PEG and 20 kDa PEG). STZ-rats were randomized into 3 groups (n=3 per group) and implanted with silanized (no PEG) or PEGylated (2 and 20 kDa) insulin devices subcutaneously in the interscapular tissue of the abdomen. Each animal served as its own control, and was implanted with the three different surface-treated devices, each one in a separate subcutaneous pocket. After a 15 and 30 day implantation period, animals were sacrificed and the devices with surrounding tissue were carefully explanted. Retrieved devices encapsulated with new-formed surrounding tissue were fixed in 10% buffered formalin and embedded in paraffin for histological analysis. Cross-sectioned slices were stained with HNE1, MAC2 and Mason's Trichrome to identify and quantify immune cells, macrophage recruitment and collagen capsule thickness, respectively. To determine membrane degradation, explanted devices were fixed with buffered formalin and surface morphology was analyzed by environmental scanning electron microscopy (eSEM, Hitachi S3400 microscope, Japan, 15 kV). Wet devices were directly fixed onto a cold stage sample holder with double-sided carbon tape, and frozen at −24° C. under 90 Pa. Histology was performed by Dr. Hibret Adissu and tissue preparation and analysis were performed by the CMHD Pathology Core Laboratory at Mount Sinai Hospital, Toronto, Canada.

In Vivo Glucose-Responsiveness of the Device—Glucose Challenge Test:

Long chain (20 kDa) PEG-treated microdevices were implanted in STZ-rats as described above (3 devices per animal, n=5) and allowed to rest for 72 hrs to confirm the decrease of blood glucose (BG) to normal levels by the insulin release from the implant. One hour prior to the experiment, food was removed from rat cages to prevent confounding glycemic overlap. Rats were given an intraperitoneal injection of glucose (1 g·$kg^{-1}$, 50% dextrose), and their BG levels were continuously monitored during 90 min using a One Touch glucometer (LifeScan, Inc., Johnson & Johnson) with blood samples taken from the tail vein. At the end of the experiment food was returned to the cages, and animals were allowed to rest for 24 hrs. The experiment was repeated with the same group of animals for three consecutive days. Non-diabetic healthy animals were used as controls for comparison (n=3).

In Vivo Long-Term Efficacy of the Microdevice:

STZ-rats were implanted with 20 kDa PEG microdevices as described above (3 devices per animal, n=5). Blood samples were collected daily from the tail vein to determine fed BG and plasma insulin levels. After 21 days, microdevices were surgically retrieved and animals were maintained for further post-implantation BG measurements. Collected blood samples were assayed to determine insulin levels using an antibody radioimmunoassay kit specific for rat insulin (Linco Research Inc., USA (the assay kit was used according to manufacturer's instructions)). Diabetic rats without implants were used as controls (n=3).

Statistical Analysis:

Student's t-test or ANOVA followed by Tukey t-test (OriginPro8©) were utilized to determine statistical significance between two or more groups, respectively. A p value<0.05 was considered to be statistically significant.

Results

Effect of PEG Chain Length on the Glucose-Responsive Insulin Release of the Microdevice:

Different PEG coatings were applied to the membrane surface, short chain length (mPEG MW 2 kDa) and long chain length (mPEG MW 20 kDa). PEGylation of the device was performed by directly coupling the carboxyl groups of an activated PEG derivative (NPC-activated PEG) with the amine surfaces of the device.

Figure 11:
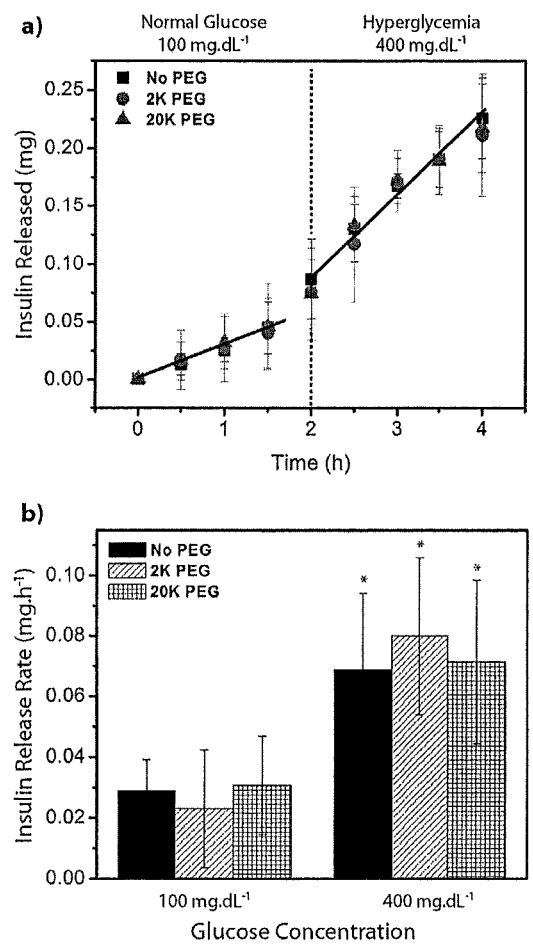
FIG. 11 graphically illustrates (a) insulin release over normal and hyperglycemic glucose concentrations for microdevices prepared without PEG treatment (no PEG, ■) and with PEG treatment (2K PEG and 20K PEG, ▲), and (b) rate of insulin release (mg·$h^{-1}$) as a function of glucose concentration, calculated from the slopes of the curves. Error bars represent standard deviation (n=5). Difference between normal to hyperglycemic insulin release rate was statistically significant (p<0.05)

With the modification of the device by PEGylation, one concern was that the chemical treatment would compromise the ability of the membrane to respond fast to glucose changes in the environment. To answer this question, in vitro glucose-responsiveness of devices prepared with 2 kDa and 20 kDa PEG was compared to control devices that did not undergo any surface modification (no PEG). The glucose-responsiveness of the devices was determined by monitoring the in vitro release of insulin as a function of time and glucose levels. Glucose levels in the release buffer were changed from clinically relevant ranges of 100 mg·dL$^{-1}$ (normal) to 400 mg·dL$^{-1}$ (hyperglycemia) at pre-determined times. From the plots comparing the insulin release profiles of the three groups (FIG. 11a/b), the ratios of insulin release at hyperglycemia versus normal glucose were all above two-fold ($R_{400}$/$R_{100}$) (Table 1). As well, the change in insulin release occurred rapidly, with the insulin release rates increasing almost immediately after glucose increase, in all three groups. Thus, the microdevice modifications from PEG surface grafting did not show a significant difference or trend in insulin release profiles as a result of PEG surface grafting. Insulin formulation remained stable within devices and did not fibrillate or aggregate within the reservoir due to the hydrophilic surface treatment.

TABLE 1

Release rate of insulin from PEGylated microdevices

|  | No PEG | 2 kDa PEG | 20 kDa PEG |
|---|---|---|---|
| $R_{100}$ (mg · h$^{-1}$) | 0.29 | 0.22 | 0.31 |
| $R_{400}$ (mg · h$^{-1}$) | 0.69 | 0.8 | 0.71 |
| $R_{400}/R_{100}$ | 2.37 | 3.64 | 2.29 |

Effect of PEG Chain Length on Biocompatibility of the Microdevice:

Long-chain PEG (20 kDa) were utilized to generate a brush-like layer on the microdevice surfaces to create a stearic barrier against excess cellular adhesion and both acute and chronic immune response. PEG 20 kDa was tested to determine improvement in biocompatibility and microdevice integrity compared with 2K PEG layers, and biocompatibility effect of short and long-chain PEG-treated microdevices for subcutaneous implantation in the abdomen. For the study, rats were subcutaneously implanted with microdevices (no PEG, 2 kDa and 20 kDa) for 15 and 30 days. Histological analysis of surrounding tissue around the microdevices showed that all three treatment groups led to the growth of a fibrous capsule around the implant; however, each group showed very different levels of capsule thickness, immune response and cell types. The results (Table 2) showed a clear effect of the device surface on the response of the host to the implant. A reduction of inflammation and fibrosis (tissue encapsulation of the device) was observed in the order 20 kDa PEG>2 kDa PEG>no PEG.

Capsule thickness was greatest for animals implanted with no PEG microdevices, up to 1000 µm (15 days implantation) and 100-400 µm (30 days implantation). For this same group, after 15 days implantation, heavy inflammation was seen near the internal capsule walls, characterized by dark purple staining from active neutrophil recruitment. Large plasma cells and immature fibroblasts were characteristic of localized and continuous inflammation as well. Inflammation was heavily pronounced after 30 days implantation and numerous eosinophils and vasculature were also present. The heavy recruitment of eosinophils indicates a strong allergy-mediated reaction (immune response) caused by the implant.

In contrast, PEGylated devices showed thinner fibrous capsule, lower inflammation and little to no allergic reaction. Devices treated with 2 kDa PEG showed a thinner fibrous capsule with presence of wavy, mature collagen matrix, 100-300 µm (15 days) and up to 400 µm (30 days). For this group under HNE1 staining, some darkly stained, inflammatory-mediated neutrophil recruitment was still present closest to internal lumen, but eosinophil and vasculature presence was markedly reduced, indicating lower allergic response, as compared to no PEG devices. Capsule thickness was further reduced for devices treated with 20 kDa PEG (<100 um) at both timepoints, and much more uniform across the entire cross-section. Internal neutrophil recruitment was minimal compared with no PEG and 2 kDa PEG samples with no significant presence of eosinophils, suggesting very low or absent inflammation and allergic response. All three groups showed presence of plump plasma cells, an indicator of chronic immune response to foreign material, but are not highly active in cell recruitment and inflammatory response.

TABLE 2

In vivo comparison of PEG surface treatments to immune parameters.

| Implantation period | Diagnosis | Surface Treatment | | |
|---|---|---|---|---|
| | | No PEG | 2 kDa PEG | 20 kDa PEG |
| 15 days | Capsule thickness | 1000 µm | 100-300 µm | 50-150 µm |
| | Capsule composition | Mononuclear inflammatory cells (mainly macrophages) | Mature fibrosis with some infiltration of macrophages, lymphocytes and plasma cells. | Thin layer of fibrosis and fibroplasia with low numbers of macrophages and lymphocytes. |
| | Inflammation | Extensive | Extensive | Mild |
| | Immune response | Mild, occasional eosinophils | Low, occasional eosinophils | Low, occasional eosinophils |
| 30 days | Capsule thickness | 100-500 µm | 30-500 µm | 30-50 µm |
| | Capsule composition | Mature fibrosis with large infiltration of macrophages, lymphocytes and plasma cells. | Mature fibrosis with infiltration of macrophages, lymphocytes and plasma cells. | Mature fibrosis with fibrocytes embedded in abundant collagen. |
| | Inflammation | Severe | Mild | Minimal |
| | Immune response | Extensive, large infiltration of eosinophils in fibrous capsule/surrounding tissue. | Low, minimal infiltration of eosinophils in the fibrous capsule. | Absent, extremely rare eosinophils. |

Effect of PEG Chain Length on Bioinorganic Membrane Morphology and Cell Adhesion:

For long-term applications, it is important that the device causes minimal response to the host and also that the implant shows low degradation rates in vivo, particularly minimal degradation of the glucose-responsive membrane. In order to evaluate the effect of the surface treatments on the in vivo degradation of the membrane, devices retrieved from animals after 15 and 30 days implantation period were fixed with formalin and surface morphology was analyzed by environmental scanning electron microscopy (eSEM).

Before implantation (Day 0), devices showed no differences on membrane morphology and integrity as expected between the three groups. After 15 days, cell attachment was present on both no PEG and 2 kDa PEGylated devices, with higher cell attachment and agglomeration observed for the non-PEGylated device. Negligible cell attachment was seen on the 20 kDa PEGylated devices, an indication of good resistance to initial non-specific protein attachment and subsequent cascade response. As well, some cellular and protein adhesion on the silicone tubing was easily visible in the no PEG devices, while little adhesion was observed for both PEGylated samples. After 30 days, complete central degradation of the membrane was observed in no PEG devices, with integrity of the permeable membrane compromised and heavy cellular and tissue adhesion throughout the surface. Compared to no PEG, devices treated with 2 kDa PEG showed lower membrane degradation and cellular attachment. However, the 2 kDa surface treatment did not completely prevent intense cell attachment on the membrane surface and the adjacent silicone tubing. Even lower cellular attachment was observed for devices treated with 20 kDa PEG. More importantly, for this group the images revealed that the integrity of the membrane was not compromised after 30 days implantation. Little or no cellular adhesion was observed on the silicone surface adjacent to the membrane, showing a clear improvement of the addition of PEG to the silanized surface as well as to the addition of increased PEG chain length.

The eSEM results are in agreement with the observations obtained through histological analysis, which shows that the PEG treatment can greatly decrease cellular adhesion on the device surfaces in the order 20 kDa PEG>2 kDa PEG>no PEG. Preventing recruitment of downstream immune cells and inflammatory-mediated cytokines relieves the degradation stresses towards the bioinorganic membrane. Thus, devices PEGylated with 20 kDa PEG exhibited improved biocompatibility and decreased degradation, with negligible effect on glucose-responsiveness.

Figure 12:
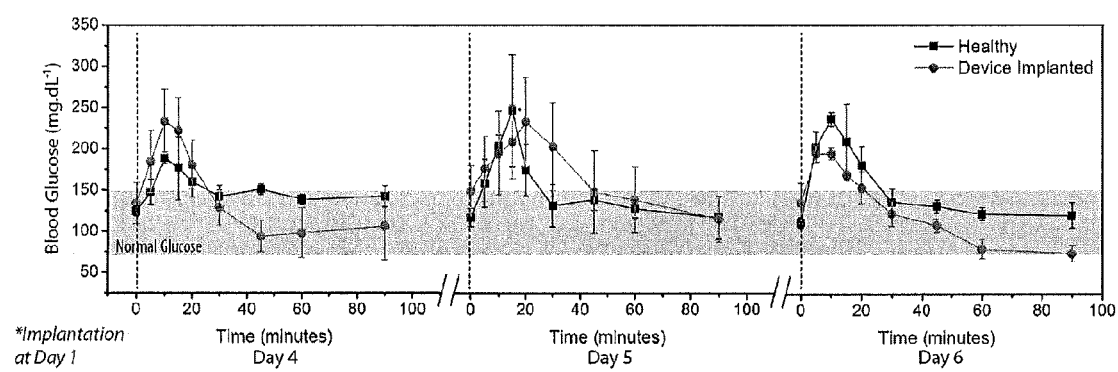
FIG. 12 graphically illustrates multiple cycle glucose challenge testing for healthy (■) and device-implanted diabetic Sprague-Dawley rats (●). Rats were fed for 12 hours in between glucose challenge cycles and fasted one hour before glucose injection until the end of test. Error bars represent standard deviation (n=3)

Long Chain PEG-Treated Microdevices Show Multiple Cycle Glucose-Responsiveness In Vivo:

An ideal closed-loop insulin device should be able to release more or less insulin in response to real time glucose changes in vivo, similarly to healthy beta cells. In previous work we have demonstrated that insulin microdevices implanted i.p. have shown efficacy in vivo for over 5 days and lead to rapid decrease of plasma glucose levels in response to a short-term glucose challenge. It was investigated whether or not microdevices implanted subcutaneously would present a similar in vivo glucose responsiveness profile and maintain this activity over several cycles. We also wanted to compare the responsiveness of the device to the healthy pancreas. For this, short term in vivo device performance was determined by monitoring blood glucose of implanted animals over an acute time period immediately after glucose bolus injection, to simulate meal-time glucose challenge and glycemic response. The same experiment was performed simultaneously in healthy animals for comparison purposes. Ideal glycemic response would minimize hyperglycemic period and return to euglycemia within 30-60 minutes. Multiple cycles over separate days were performed to determine consistency in microdevice glucose response. These results are presented in FIG. 12.

Figure 13:
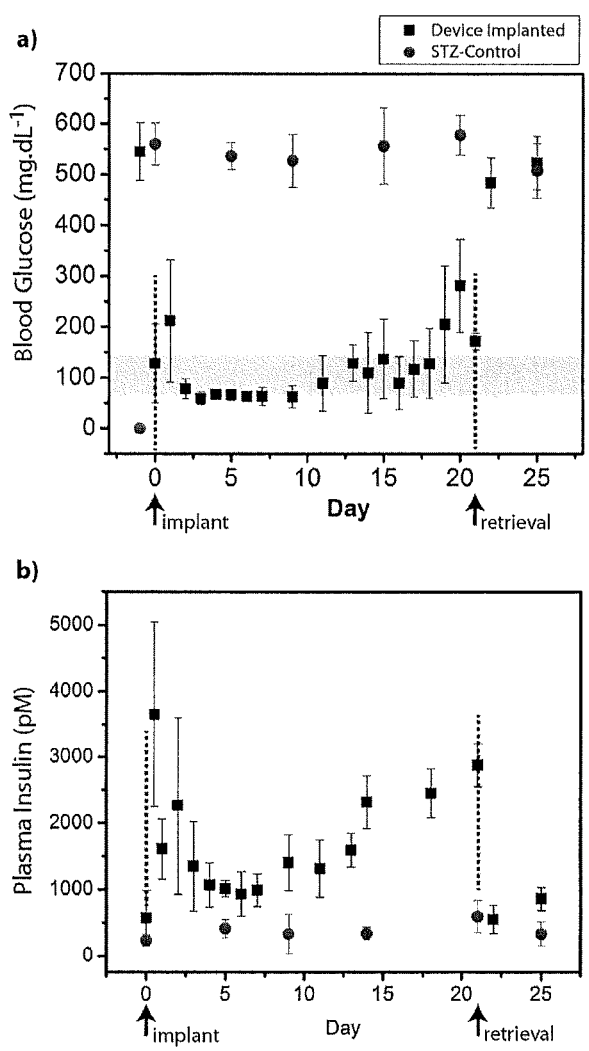
FIG. 13 graphically illustrates in vivo performance of subcutaneously implanted insulin microdevices in STZ-diabetic rats. Microdevices implanted at day 0 and retrieved at day 21. Blood glucose (a) and insulin (b) were taken via test strip and blood sample assay, respectively. Error bars represent standard deviation (n=5)

Long-Chain PEGylated Microdevices Show Long-Term In Vivo Efficacy:

Finally, it was determined whether or not the optimization of the device would lead to prolonged efficacy for the control of blood glucose in vivo. Long-term in vivo microdevice performance was determined by monitoring glycemia and plasma insulin in subcutaneously implanted diabetic rats over 28 days. As shown in FIG. 13a, diabetic rats showed very high glucose levels as expected (>500 mg·dL$^{-1}$) throughout the duration of the experiment. In contrast, animals implanted with insulin microdevices (treated with 20 kDa PEG) showed an immediate decrease in blood glucose levels from hyperglycemic (>500 mg·dL$^{-1}$) to normal (75-140 mg·dL$^{-1}$) within 24 h. Normoglycemia was maintained over 18 days, without evident episodes of hypo or hyperglycemia. After 18 days, glucose levels increased outside of normal range (~180-270 mg·dL$^{-1}$), however it was still significantly lower than levels observed in the control rats. Upon device removal from implanted rats, blood glucose returned to hyperglycemic levels, confirming glycemic control was provided by the insulin microdevice. Analysis of plasma insulin levels (FIG. 13b) shows initial increase post-surgery, but steady levels throughout the duration of the experiment. Moreover, upon insulin microdevice removal, insulin levels dropped to pre-implantation levels, showing no endogenous insulin production having an effect on glycemic levels, indicating circulating insulin was provided solely from the microdevices. All rats were healthy in the insulin microdevice implanted group throughout the duration of the experiment, with slight weight gain over time.

Conclusions

The long chain PEG treatment provided an improved glucose-responsive insulin delivery microdevice and achieved 18 day in vivo efficacy with subcutaneous implantation. A desirable glycemic profile with minimal hyper or hypoglycemic episodes was obtained. The long chain PEG treatment improved biocompatibility of the device significantly with minimal tissue encapsulation, inflammation and immune responses. Glucose tolerance testing on diabetic rats over three cycles on different days showed rapid response to glucose challenge and effective glycemia-regulating capability of the implanted devices, similar to healthy animals.

Example 12

Effect of PEGylation on In Vivo Performance of the Insulin Delivery Device

Materials

Ethylene-vinyl acetate copolymer resin (ELVAX-40W; EVAC) was provided by E. I. Du Pont (USA). Polydimethylsiloxane (PDMS, Sylgard 184) was purchased from Dow Corning Corporation (USA). S1805 photoresist, SU-8 photoresist and SU-8 developer (1-Methoxy-2-propyl acetate) were purchased from Microchem (USA).

Preparation of the Microporous Membrane

Figure 14:
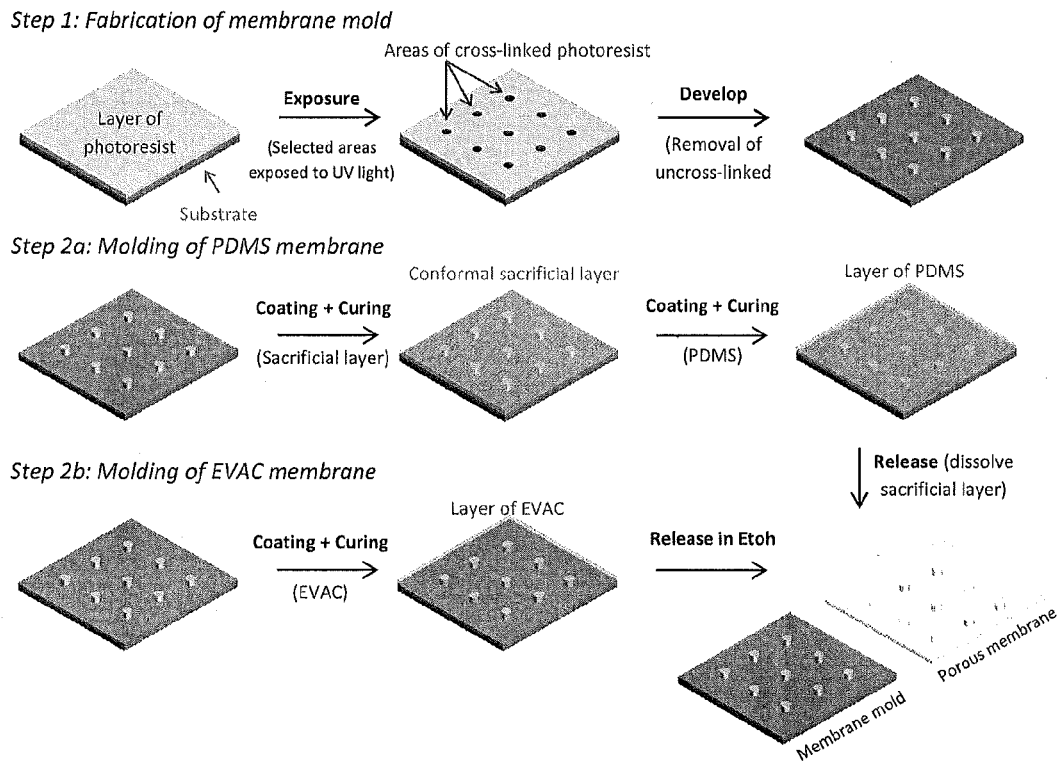
FIG. 14 is a schematic illustrating the process for fabricating microporous PDMS membranes (a) and illustrating embodiments of the device with and without (bare) a protective membrane (b)
Figure 14:
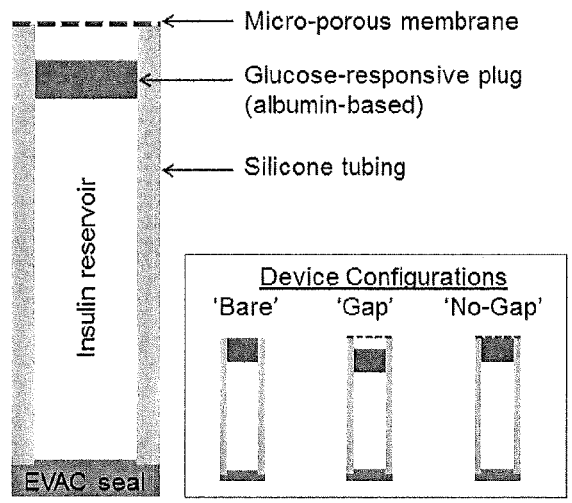

A microporous membrane replica mold was constructed using standard microfabrication methods (FIG. 14). A 60 μm thick layer of SU-8 50 was spin coated onto a silicon wafer substrate and soft-baked at 65° C. and 95° C. for 1 and 5 minutes respectively. Arrays of 60 μm tall free-standing pillars were formed by selective photo polymerization of the SU-8 layer using photolithography followed by a post-exposure bake at 65° C. and 95° C. for 1 and 5 minutes respectively. Uncrosslinked SU-8 was subsequently removed using SU-8 developer. The replica mold was rinsed with isopropyl alcohol, DDI water, and dried under nitrogen. A final hardbake procedure was performed at 170° C. for 4 hours. Separate replica molds were fabricated with 10 μm, 20 μm, and 60 μm post diameters.

Microporous PDMS membranes were replica molded from the SU-8 templates (FIG. 14). To enable self-release of the membrane from the template, the replica mold was first coated with a 1 μm thick sacrificial layer of Shipley S1805 positive photoresist. Following a 90 s bake at 120° C., PDMS pre-polymer mix (1:10 ratio of polymer to cross-linker) was spin-coated onto the mold and cured at 120° C. for 5 minutes. After scoring the wafer edges, release of the microporous PDMS membrane was achieved by soaking the entire mold in acetone. The floating PDMS membrane was transferred onto a sheet of aluminum foil for subsequent handling. Individual porous membranes were bonded to silicone tubing at 120° C. after treatment with oxygen plasma.

The glucose-responsive device was prepared as described above. Three different device configurations, based on the relative position of the hydrogel plug, were produced (FIG. 14b): (1) bare device: an unprotected device in which the glucose-responsive membrane is placed at the tip of tube, (2) gap device: a membrane protected device in which a gap separates the glucose-responsive membrane and the porous PDMS membrane, and (3) no-gap device: a membrane-protected device in which the glucose-responsive membrane is placed in contact with the porous PDMS membrane. Glucose-responsive hydrogel devices were stored pH 7.4 PBS at 4° C. The open end of the tubing was sealed with EVAC solution (8% in dichloromethane (w/v)) and allowed to dry in air to form a solid round cap over the tubing end.

mPEG (poly(ethylene glycol) methyl ether, 20 kDa) was activated with 4-nitrophenyl chloroformate (NPC) as described above. Silanized devices were incubated in and filled with activated PEG solution (0.01 M activated PEG in pH 7.4 PBS) for 48 h at 4° C. to ensure modification of all device surfaces. Devices were extensively washed with DDI water and kept in pH 7.4 PBS at 4° C. prior to use.

The effect of the microporous membrane on device biocompatibility was evaluated in STZ-induced diabetic adult male Sprague-Dawley rats (300-350 g, Charles River Laboratories, Raleigh, N.C., USA) using procedures described above. STZ was administered at a dose of 65 mg/kg via the tail vein 1 week prior to implantation to induce type I diabetes in the rats. Just prior to implantation, all sterile implants were filled with insulin formulation and stored in sterile saline. Devices were implanted subcutaneously in the periscapular region of the dorsum. Implantation at this site compared to the abdominal area ensured that the rats would be unable to introduce contamination to the implantation wound. Four separate 0.5 cm incisions were made in the skin. Subcutaneous pockets were created at the site of each incision using blunt dissection. Each subcutaneous pocket received one of the following implants: device with a 10, 20, or 60 μm diameter protective membrane, or an unprotected device (no porous protective membrane). The wounds were sutured with absorbable sutures. Blood glucose levels were monitored pre-surgery and post-surgery to ensure that the rats recovered properly and did not suffer from sever hypoglycemia.

Rats were sacrificed at 3, 7, 14, and 30 days post-surgery with $CO_2$ and cervical dislocation. The implants were removed with the surrounding tissue and placed in a fixative solution. Samples to be analyzed under eSEM were fixed in universal fix (1.0% gluteraldehyde, 4.0% formaldehyde in 0.1M phosphate buffer) for 24 h, incubated in osmium for 5 minutes, and cut to expose the glucose-responsive membrane. Samples for histological analysis were fixed in 10% buffered formalin for 24 h, embedded in paraffin, sectioned into 5 μm-thick slices, and stained with hematoxylin & eosin (H&E), Mason's Trichrome and CD31 immunohistochemical stain.

Biocompatibility of each implant was evaluated based on degradation of the glucose-responsive membrane, fibrous capsule thickness, presence and abundance of inflammatory cells, and peri-implant angiogenesis. Degradation of the glucose-responsive membrane was analyzed using eSEM. Fibrous capsule thickness measured both at and away from the implant opening was quantified from trichrome-stained tissue samples. The fibrous capsule was defined as the region of dense collagen adjacent to the implant surface. The abundance of macrophages, neutrophils, fibroblasts, and lymphocytes within each sample was determined from H&E stained tissue samples by a certified veterinary pathologist. Data is expressed as mean values +/− standard deviation and was analyzed for significance ($p<0.05$) with a student's t-test.

The effect of the microporous membrane on device lifetime was evaluated in STZ-induced diabetic adult male Sprague-Dawley rats (300-350 g, Charles River Laboratories, Raleigh, N.C., USA). A one 1 cm midline incision was made in the lower abdomen followed by blunt dissection to create subcutaneous pockets for device implantation. The rats were separated into 3 groups, with each group receiving one of the following implants: Four membrane-protected devices (60 μM pore diameter), four bare devices (no protective porous membrane), or four sham devices (sterilized silicone tubing) which served as control. Blood glucose levels were measured pre-surgery and post-surgery to ensure that the rats recovered properly and did not suffer from severe hypoglycemia. Rats were housed individually on a reverse light-cycle and were given ad libitum access to food and water. Blood glucose levels were monitored daily using a OneTouch® Ultra® glucose meter. Similarly, blood insulin and c-peptide levels were measured once daily at 6 pm. Plasma insulin and C-peptide level was determined using an antibody radioimmunoassay kit specific for rat insulin (Linco Research Inc., USA) according to the manufacturer's instructions. Rat weight and health was monitored regularly for the duration of the study. Insulin sensitivity in the diabetic rats were measured both prior to implantation and after the loss of device efficacy. 0.5 IU of insulin was administered subcutaneously followed by intermittent blood glucose measurements to monitor the resulting decrease in blood glucose level. Comparison of insulin sensitivity prior to implantation and post-efficacy was used to determine whether the rats had developed insulin resistance over the course of the study.

Results

In Vivo Biocompatibility (Device Degradation)

Environmental SEM imaging was used to assess the effect of device configuration (e.g. bare, gap, and no-gap devices) and membrane geometry (10 μm, 20 μm, and 60 μm pore sizes) on phagocytic cell accumulation at the active implant surface, and the resulting cell-mediated degradation of the glucose-responsive plug. Devices explanted at day 3, 7, 14 and 30 following implantation were fixed and sectioned longitudinally for eSEM imaging.

The effect of device configurations ('bare', 'gap', and 'no-gap' devices) on cell infiltration and degradation of the glucose-responsive hydrogel plug was determined at day 3 and day 7. Bare devices without the protection of the microporous membrane exhibited early signs of cell-mediated degradation at day 3 as evident from the slightly resorbed glucose-responsive plug surface. Progression of this process results in appreciable cell recruitment at the glucose-responsive plug surface, formation of a loose fibrous matrix, and significant resorption of the glucose-responsive plug by day 7. Use of a microporous membrane directly in contact with the glucose-responsive plug prevented plug resorption at day 3, however considerable cell infiltration and degradation of the plug is observed at day 7. This may be due to the close proximity of the glucose-responsive plug to the exterior of the device where the plug serves as a matrix through which recruited inflammatory cells are able to migrate across unimpeded.

In contrast, when the glucose-responsive plug and the microporous membrane were separated with a small gap, few inflammatory cells accumulated on the glucose-responsive plug and no signs of cell-mediated degradation were observed at days 3 or 7. Thus the gap between the microporous membrane and the glucose-responsive plug is critical for minimizing cellular migration to the active implant surface and subsequent degradation. The presence of cells on the underside of the microporous membrane shows the ability of the inflammatory cells to pass through the micron-sized pores. Surprisingly, these cells remain on the underside of the microporous membrane and preferentially aggregate at the device corners where they eventually produce a loose fibrous matrix by day 7. Degradation of the glucose-responsive membrane in the bare and no-gap devices is clearly evident, while the gap device remains intact.

The influence of microporous membrane pore size on cell migration and cell-mediated degradation of the glucose responsive plug over a 30 day period was then assessed. For 10 μm and 20 μm pore sizes, no cells are found residing on the glucose-responsive plug at days 7 and 14. This contrasts to 60 μm pore membranes in which a small number of cells are found on the glucose-responsive plug, however no signs of plug resorption are observed. By day 30, a number of inflammatory cells and some fibrous material can be observed on the glucose responsive plug for all three membrane pore diameters, however the plugs are not blanketed with cells, as is the case of the day 7 bare device, and resorption of the plug is not apparent. Inflammatory cells can be seen along the inner tube wall as a means to migrating towards the glucose-responsive membrane.

In Vivo Biocompatibility (Fibrous Capsule Formation)

Devices with and without a microporous protective membrane were implanted subcutaneously in diabetic rats for up to 30 days. Subcutaneous inflammation around the explanted device was evaluated histologically using H&E and Mason's trichrome stains to identify inflammatory cells and collagen fibers, respectively. Immunohistochemistry was used to stain for the CD68 antigen, a marker for resident macrophages. Sections were scored for total CD68+ cells containing one nucleus (macrophages), and fused multinucleated CD68+ cells (FBGCs). The fibrous capsule thickness and abundance of inflammatory cells around the implant was quantified as a standard measure of chronic inflammation to synthetic implants.

Subcutaneous inflammation and fibrous capsule formation around bare and microporous membrane-protected gap devices (60 μm diameter pores) were compared over a 30 day period, at the device opening. At day 3, bare devices elicited a focal, mononuclear (lymphocytes and histocytes) and mild neutrophilic reaction admixed with mild fibroplasia (~80 μm thick) at the device opening. Few activated blood vessels are found within the organizing fibrous capsule. By day 7, there is markedly thicker fibrous capsule (~500 μm) and increased granulation tissue surrounding the implant cavity and extending up to 2 mm into the surrounding tissue. The granulation tissue is characterized by numerous dilated and activated blood vessels, as well as numerous perivascular macrophages and lymphocytes. The collagen found surrounding the implant site is noticeably more organized compared to day 3. While the inflammation at day 3 and 7 is a mild lymphocytic, histocytic and neutrophilic response, by day 14 and 30 a severe lymphoplasmacytic inflammation dominated by plasma cells, lymphocytes and macrophages is observed. At day 14, the fibrous capsule thickness at the implant opening increased to >1000 μM and by day 30 the fibrous capsule and a number of inflammatory cells can be seen infiltrating into the glucose-responsive plug.

Devices protected with a microporous membrane elicited a milder inflammatory response at all time points compared to bare devices in terms of the number and type of inflammatory cells present, and the fibrous capsule thickness. Early subcutaneous inflammation around the implant is lymphocytic, histocytic and neutrophilic at days 3 and 7. By day 30 inflammation is resolved as evidenced by minimal residual perivascular lymphocytic and histocytic inflammation, absence of neutrophils at the implant site, and a well-defined fibrous capsule (<100 μm) suggesting that the device is likely tolerable for a prolonged period of time. This contrasts with bare-device controls where a prominent lymphoplasmacytic inflammation is observed at days 14 and 30 suggesting persistent immune response. Earlier vascular proliferation and increased collagen organization is also observed around the membrane-protected devices (day 3) compared to bare-device control (day 7).

For both bare and microporous membrane protected devices and at all time points, the fibrosis distal from the implant opening is considerably milder with thinner fibrous capsules and fewer inflammatory cells compared to the inflammation found adjacent to the glucose-responsive membrane.

The effect of pore diameter on implant fibrous encapsulation after a 30-day implantation period was assessed. Bare devices elicited a prominent lymphoplasmacytic inflammation, infiltration of inflammatory cells into the device reservoir, and the formation of a thick capsule at the device entrance (>600 microns). This contrasts to the minimal inflammation (lymphocytic and histocytic) and relatively thin and well-defined fibrous capsule found around all membrane-protected devices (<100 micron) at day 30. The capsules in each case are largely void of inflammatory cells and show a similar morphology in terms of cell number, type and fiber organization. Thus the inflammatory response around all membrane-protected devices was resolved by day 30, irrespective of pore size. Differences in fibrous capsule thickness were observed between the various membrane pore sizes, with 60 μm and 20 μm pore diameter membranes exhibiting a relatively thicker fibrous capsule (~100 μm) compared to those formed around 10 μm pore diameter membranes (~30 μm).

In Vitro Device Characterization

Figure 15:
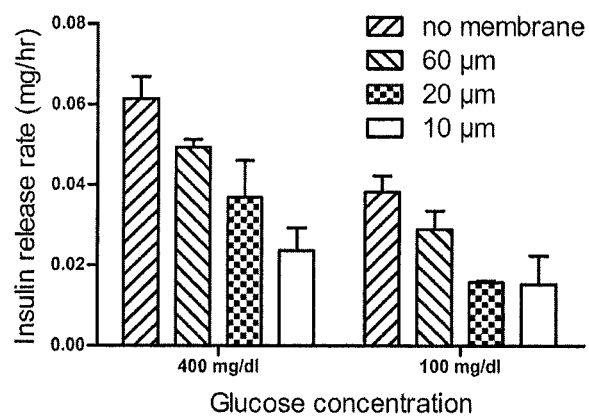
FIG. 15 graphically illustrates (a) in vitro insulin release at two different glucose concentrations (100 mg/dL, and 400 mg/dL) from bare devices and membrane-protected devices with 60 μm, 20 μm, and 10 μm pore diameters (n=4); (b) as well as a far-UV spectrum of released insulin measured using circular dichroism (CD) spectroscopy.
Figure 15:
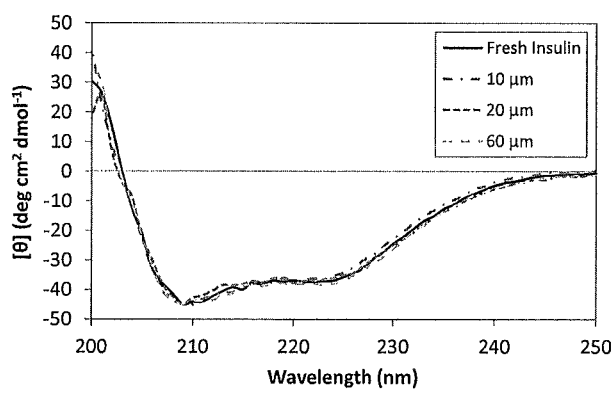

The effect of microporous membrane pore size on insulin release under normal (100 mg/dL dextrose) and hyperglycemic (400 mg/dL dextrose) conditions was quantified in vitro using UV/Vis spectroscopy (FIG. 15a). The glucose-responsive insulin release rate of the 'bare' device was also quantified. Incorporation of the microporous membranes decreased the insulin release rate of the devices by as much as 60% in the case of membranes with 10 μm diameter pores. However all devices maintained an elevated insulin release rate under hyperglycemic conditions compared to euglycemic conditions. The responsiveness of the membrane-protected devices ($R_{400/100}$), defined as the ratio of the rate of insulin release at elevated glucose levels to the rate of insulin release at normal glucose levels, are comparable to that of the bare device as shown in Table 3, indicating that incorporation of the microporous membranes did not adversely affect device glucose sensitivity.

TABLE 3

| Membrane pore diameter (μm) | Permeation area (μm$^2$) | Responsiveness ($R_{400/100}$) |
|---|---|---|
| No membrane | 80.42 × 10$^5$ | 1.61 ± 0.29 |
| 60 μm pore diam. | 1.12 × 10$^5$ | 1.70 ± 0.21 |
| 20 μm pore diam. | 1.11 × 10$^5$ | 2.33 ± 0.53 |
| 10 μm pore diam. | 1.12 × 10$^5$ | 1.55 ± 0.46 |

As released insulin may interact with the porous protective membrane surface, CD analysis was performed to verify the structural integrity of the released insulin. Far-UV CD spectral analysis of the released insulin revealed a characteristic double peak consistent with alpha-helical proteins (FIG. 15b). The spectrum of device-release insulin also overlapped with that of fresh insulin. These results suggest that membrane-protected devices do not adversely affect the structure or function of insulin.

In Vivo Efficacy

Figure 16:
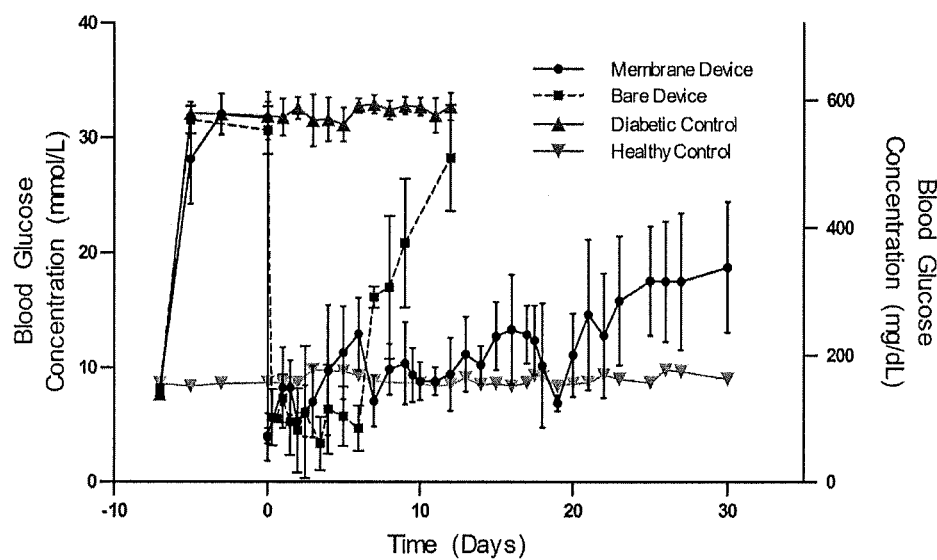
FIG. 16 graphically illustrates a) blood glucose over the course of 30 days after implantation with saline-filled devices (control), unprotected insulin-filled devices (bare), and microporous membrane-protected insulin-filled devices (membrane gap device with 60 μm pore diameter) including a comparison with blood glucose levels from healthy non-diabetic rats; and (b) plasma insulin levels over the course of 30 days after implantation with control, bare and membrane-protected devices. Data points represent mean±SD (n=3). Student's t-test: *$p<0.05$.
Figure 16:
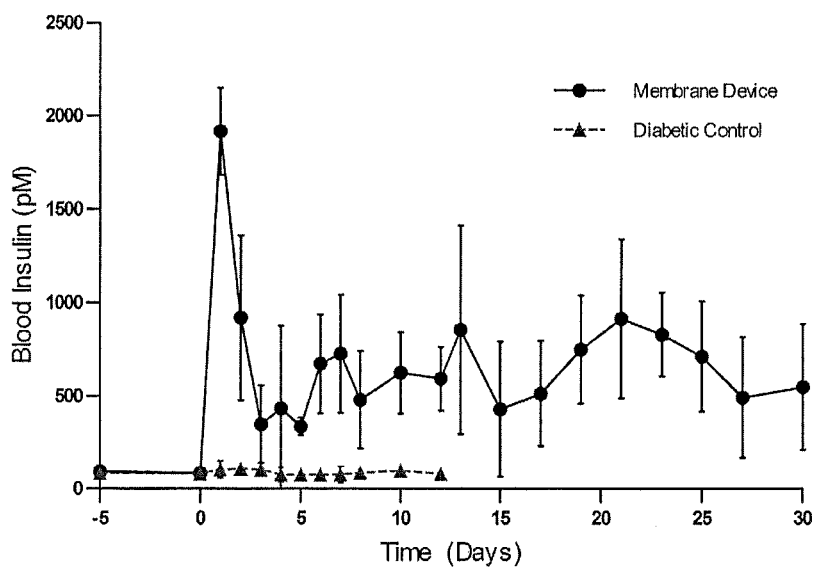

To assess whether the improvements to implant biocompatibility resulting from the use of a microporous protective membrane translated to prolonged device efficacy, gap devices featuring a 60 μm pore diameter PDMS membrane were implanted into the subcutaneous abdomen of STZ-induced diabetic rats. Fed-state blood glucose and plasma insulin levels were measured over a 30-day period (FIG. 16). Plasma c-peptide levels were consistently below 150 μM over the duration of the study.

Healthy control rats maintained a normal blood glucose level of ~8 mg/dL (FIG. 16a). Following STZ administration, diabetic rats maintained an elevated blood glucose level of >30 mg/dL. Implantation of bare devices resulted in normal blood glucose levels for 6 days followed by a sharp return to hyperglycemia. Implantation of 60 μm pore diameter membrane-protected devices regulated blood glucose levels in the diabetic rats over a 21-day period followed by a gradual onset of hyperglycemia. Blood insulin levels in the diabetic rats were significantly elevated immediately following membrane device implantation followed by a steady insulin level of 400-800 μM for 30 days (FIG. 16c). Therefore the gradual increase in blood glucose levels over the 30-day period may be attributed to the gradual increase in animal weight over time or to a decrease in reservoir insulin activity over time.

Conclusions

Biocompatible polymeric membranes featuring micron-sized pores minimized cell accumulation at the glucose-responsive plug surface and subsequent cell-mediated degradation. Use of the membranes, particularly membranes spaced from the plug surface, further resulted in resolution of the inflammatory process to the implant as evidenced by minimal residual perivascular lymphocytic and histocytic inflammation, absence of neutrophils at the implant site, and a well-defined fibrous capsule (<100 μm) by day 30 following implantation, suggesting that the device is likely tolerable for a prolonged period of time. This contrasts sharply with the ongoing inflammatory response surrounding the unprotected devices at day 30 post implantation.

Electron microscopy of the explanted devices demonstrated that the microporous membrane-protected devices featuring 10 μm and 20 μm pore diameters exhibited the least number of inflammatory cells at the active implant surface compared to devices with 60 μm diameter pores. Thus the membrane pore size appears to be an important factor in dictating the body's foreign body response and acceptance of the implants. In spite of this, 60 μm pore diameter membranes appear to be well tolerated by the body compared to bare devices with no protective microporous membrane. The membrane-protected devices exhibited little to no degradation of the glucose-responsive hydrogel plug for up to 30 days following implantation, irrespective of pore size. Histological examination of the explants further revealed a decrease in fibrous capsule thickness, reduced numbers of inflammatory cells around the microporous membrane-protected devices 30 days after implantation when compared to bare control devices.

The observed improvements in biocompatibility of the microporous membrane protected implant may be attributed to a passive mechanism different from prevention of protein adsorption and cell size exclusion in which the topographically smooth microporous membrane and device interior prevented inflammatory cell adhesion and migration to the functional device surface. As a result, inflammatory cells are observed to form a loose provisional matrix along the interior surfaces of the implant before they are able to migrate to the immunogenic implant surface. This process is time-dependent, and is able to significantly delay and reduce cell accumulation at the implant surface for at least 30 days. Therefore the use of the microporous protective membranes was successful at prolonging the in vivo efficacy duration of the closed-loop insulin delivery implants by up to 3-fold compared to unprotected devices. This work demonstrates the importance of device geometry in minimizing cell migration to an immunogenic surface and the ability to leverage implant geometric design as a passive method to prolong implant function lifetime.

Example 13

Preparation Glucose-Responsive Plug Containing Silica Nanoparticles

Silica nanoparticles ($SiO_2$, 10-20 nm) were added as an inorganic component to reinforce the glucose-responsive membrane or plug and additionally increase the mechanical strength of the membrane. Membranes or plugs with $SiO_2$ nanoparticles and various enzymes and poly(NIPAM/MAA) nanoparticles (NPs) content as set out in Table 4 were prepared.

TABLE 4

| Composition | Control | Silica 1 | Silica 2 | Silica 3 |
|---|---|---|---|---|
| BSA | 28 mg | 28 mg | 23 mg | 21.6 mg |
| Gox | 3 mg   5.5% | 3 mg   4.5% | 4 mg   5.9% | 4 mg   5.9% |

TABLE 4-continued

| Composition | Control | | Silica 1 | | Silica 2 | | Silica 3 | |
|---|---|---|---|---|---|---|---|---|
| CAT | 0.86 mg | | 0.86 mg | | 1.14 mg | | 1.14 mg | |
| poly (NIPAM/MAA) NPs | 17 mg | 30% | 17 mg | 25% | 21.4 mg | 32% | 24 mg | 35% |
| MnO2 | 6 mg | 11% | 6 mg | 9% | 6 mg | 9% | 6 mg | 9% |
| SiO2 | — | | 12 mg | 18% | 12 mg | 18% | 12 mg | 18% |

Typical preparation (e.g. Silica 1): In a small vial, 6 mg of powder MnO$_2$ nanoparticles was mixed with 60 uL of a 20% SiO$_2$ dispersion (DDI in 0.5 mg/ml Pluronic® F-68) and 40 uL of pH 4.8 PBS solution. The mixture was kept under ultrasonic field for 30 s by using an ultrasonic processor probe operating at approximately 100 Hz (Heischer UP100H, Germany) for dispersion of the powders. In a next step, 28 mg of BSA, 3 mg of GOx and 0.86 mg of CAT (89 uL, 10 mg/mL solution) were introduced and incubated at 37° C. for 10 min. The mixture was gently stirred for 5 min following the addition of 17 mg of poly(NIPAM/MAA) NPs (85 μL of a 200 mg/mL dispersion of in DDI water). The mixture was stirred for another 5 min, then 15 μL of glutaraldehyde (grade I, 25%) was introduced. A small volume of the mixture (2.5 uL) was immediately transferred to one end of the silanized tubing using a micropipette. The obtained plug was crosslinked at room temperature for 15 min, then rinsed with DDI water and soaked in pH 7.4 PBS solution overnight at 4° C.

Evaluation of the Membrane Morphology Using ESEM

Environmental scanning electron micrographs (ESEM) were obtained in a Hitachi S3400 microscope (Japan) at 20 kV. For evaluation of the surface morphology, as-prepared wet membranes or plugs were directly fixed onto a cold stage sample holder with double-sided carbon tape and frozen at −24.0 under 90 Pa. To study the morphology at acidic pH, membranes were soaked in DMSO/DDI 1:1 and fractured in liquid N$_2$, Cross-sections were then soaked in DDI water with pH adjusted to ~4 with HCl 1M and fixed onto a cold stage sample holder with double-sided carbon tape and frozen at −24.0 under 90 Pa.

The results showed that the rigidity is increased due to the introduction of SiO2 to the membrane formulation. The introduction of SiO$_2$ also resulted in changes on the membrane surface morphology. Higher SiO$_2$ content led to a more dense membrane backbone and smaller primary pores on the surface of the membrane. Increased rigidity and reinforcement is particularly important for membranes prepared with high content of poly(NIPAM/MAA) NPs. For membranes prepared with 35 w.t. % poly(NIPAM/MAA) NPs, for example, SiO$_2$ NPs were necessary to maintain the primary structure of the membrane upon shrinking of the pH-sensitive NPs at acidic pH. At low pH (pH<5), the absence of SiO$_2$ resulted in the collapse of the structure while for membranes prepared with SiO$_2$, a more uniform porosity was observed upon shrinking of the pH-sensitive NPs at acidic pH.

Example 14

In Vitro Glucose-Responsiveness of Insulin Devices Made with Silica-Containing Membranes Devices were made with plugs with different contents of SiO$_2$, enzymes and poly(NIPAM/MAA) NPs as described in Example 1. Devices were filled with buffered insulin solution (150 μL, 50 mg/mL) and individually placed in glass vials containing the release medium (3 mL of pH 7.4 phosphate buffer containing glucose 50 mg/dL and Pluronic® F-68 0.02 mM). Vials were sealed and kept under constant mixing in a hematology mixer. A small aliquot of the release medium (20 μL) was taken every 30 min and transferred to a 96 well microplate to determine the amount of released insulin using a BioRad protein assay. The assay was used following the manufacturer's instructions. At the end of each 2 h cycle, devices were transferred to new vials containing fresh release medium with increased glucose concentrations, 100 and 300 mg/dL, respectively, and released insulin was assayed every 30 min as described above.

The glucose-responsiveness of the insulin delivery device was defined as the ratio of the rate of insulin release (R) determined at hyperglycemic glucose (i.e., 300 mg/dL), to that at hypoglycemic and normal glucoses (50 mg/dL and 100 mg/dL), i.e., $R_{300}/R_{50}$ and $R_{300}/R_{100}$. The effect of SiO$_2$ content on the basal insulin release at hyperglycemic glucose (50 mg/dL) was calculated as a percentage of the rate of insulin release at 50 mg/dL in comparison to the control device (made without SiO$_2$).

Figure 17:
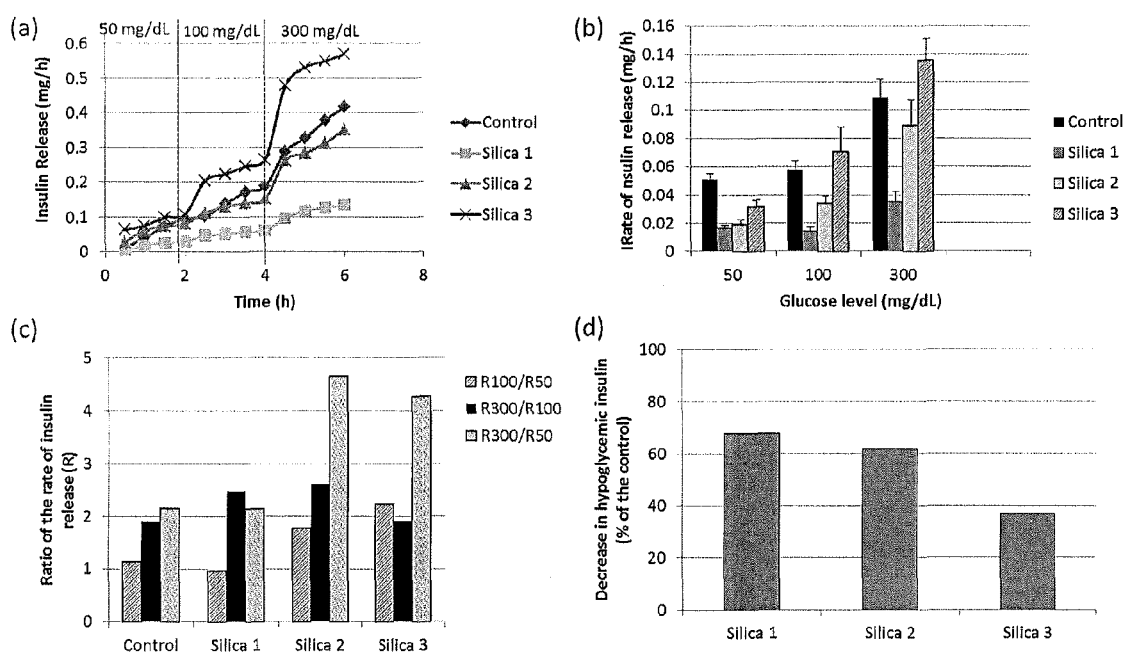
FIG. 17 graphically illustrates the effect of the $SiO_2$ nanoparticle content on the glucose-responsiveness of an insulin device. A) In vitro release of insulin over time at different glucose levels: 50, 100 and 300 mg/mL. B) Rate of insulin release (mg/h) as a function of glucose concentration, calculated from the slopes of the release curves. C) Glucose-responsiveness of the device defined as the ratio of the rate of insulin release (R) determined at hyperglycemic glucose (300 mg/dL) to that at normal (100 mg/dL) and hyperglycemic (50 mg/dL), i.e., R300/R100, R300/R50. D) Decrease in basal insulin release (hyperglycemic insulin) as compared to control devices made without $SiO_2$. Calculated from the rate of insulin release at hyperglycemic glucose (50 mg/dL). (n=5)

The in vitro results showed that the introduction of SiO$_2$ nanoparticles to the membrane formulation improved the glucose-responsiveness of the device (FIG. 17A-C) and also decreased the basal rates of insulin release at lower glucose levels (50 and 100 mg/dL) as compared to the control (FIG. 17C). By adding SiO$_2$ nanoparticles to the membrane formulation and also increasing the content of enzymes and poly(NIPAM/MAA) NPs, the rates of hypoglycemic insulin release was decreased (i.e. 62% for silica 2 membrane) while hyperglycemic insulin release was maintained at rates similar to the control (FIG. 17D).

Example 15

Figure 18:
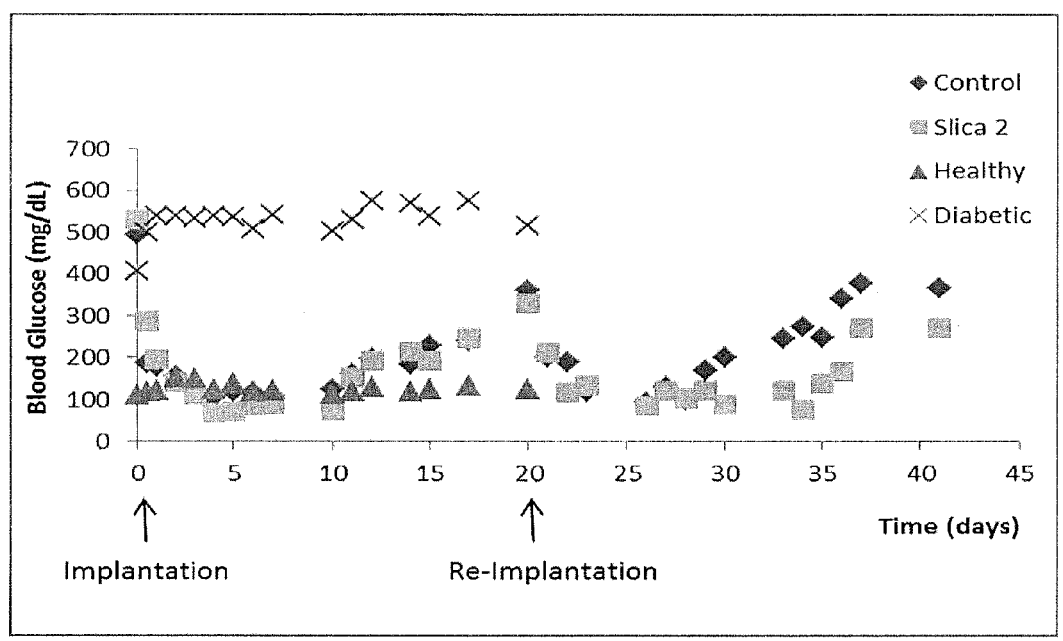
FIG. 18 graphically shows long-term in vivo efficacy of devices with membrane plugs made with or without $SiO_2$ nanoparticles. Devices were implanted at Day 0 and replaced by fresh devices at Day 20. Non-implanted diabetic and healthy rats were used as controls. (n=3-5)

In Vivo Efficacy and Glucose-Responsiveness of Insulin Devices Made with Silica-Containing Membranes The in vivo efficacy of devices made with membranes with and without SiO$_2$ was evaluated in a diabetic rat model as previously described by Gordijo et al., (Adv. Funct. Mater. 2011, 21, 73-82). In brief, control or silica 2 (see Table 4) devices were implanted subcutaneously into the abdomen of STZ-diabetic rats (3 devices per rat). The blood glucose levels of the rats were monitored daily. Both control and SiO$_2$ devices showed in vivo efficacy for up to 20 days. After a 20-day implantation period, devices were retrieved and the same animals were immediately re-implanted with new devices (3 devices per rat). Blood glucose levels of all animals were monitored up to 40 days (FIG. 18).

Figure 19:
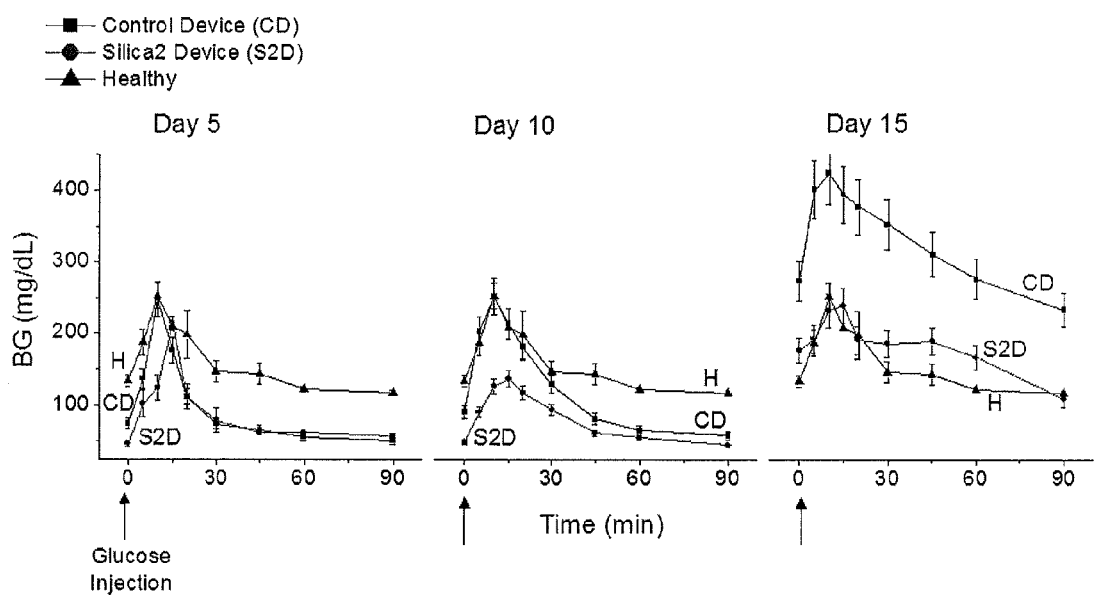
FIG. 19 graphically illustrates in vivo glucose challenge testing for rats implanted with insulin devices made with membrane plugs with and without $SiO_2$ nanoparticles for 5, 10 and 15 days (n=3-5).

To determine the glucose-responsiveness of the devices in vivo, fasting animals (1 h fasting) were challenged with intraperitoneal glucose injection (1.5 g glucose/kg rat) and blood glucose was monitored over 90 min following glucose injection. The test was performed with the same group of animals after 5, 10 and 15 days implantation period (FIG. 19). Implanted rats showed control of blood glucose in response to glucose challenge over 15 days. Implanted rats showed a similar return to normal blood glucose after glucose challenge, within 30 min, comparable to healthy rats. After 15 days, devices made with $SiO_2$ nanoparticles showed better response than control devices.

We claim:

1. A biocompatible insulin delivery device comprising a reservoir for insulin, a glucose-responsive plug that seals the reservoir, and a protective microporous membrane covering an exposed surface of the glucose-responsive plug and further sealing the reservoir, wherein the plug comprises a polymeric matrix having an inorganic component and a stimulus-responsive component adapted to alter the porosity of the plug in response to a stimulus and wherein the plug functions to release insulin from the reservoir in response to a hyperglycemic glucose concentration and to prevent insulin release from the reservoir in response to a hypoglycemic glucose concentration.

2. The device of claim 1, wherein the reservoir is made of a biocompatible material selected from the group consisting of synthetic polymer, natural polymer, metal, glass, ceramic and hybrid materials formed with biocompatible metal, glass or ceramics with one or more polymers.

3. The device of claim 1, wherein the reservoir is made of a polymer selected from the group consisting of collagen, starch blends, hyaluronic acid, alginates, carrageenan, silicone rubbers, polydimethylsiloxane, polyurethanes, acrylic polymers, poly(methyl methacrylate), polyesters, cellulose derivatives, cellulose acetate, polyethylene terephthalate, polycarbonate, polysulfone, polyvinyl chloride, polyethylene, polypropylene, polymethylacrylate and nylon.

4. The device of claim 2, wherein the material is surface modified with polyethylene glycol of at least about 2-50 kDa in size.

5. The device of claim 4, wherein the polyethylene glycol is at least about 20 kDa in size.

6. The device of claim 1, wherein the protective microporous membrane comprises a polymer selected from the group consisting of polyvinyls, polyamides, polyimides, polysulphones, polyurethanes, polyolefins, polyesters, polycarbonates, polyacrylates, polysaccharides, poly(amino acids), aramids, nylons, silicone rubbers and acrylic polymers.

7. The device of claim 6, wherein the polymer is selected from the group consisting of poly(vinyl chloride), poly(vinyl acetate), poly(ethylene-co-vinyl acetate) (EVA), poly(ethylene), poly(propylene), poly(lactic-co-glycolic acid) (PLGA), poly(methyl methacrylate) (PMMA), ethylcellulose, cellulose acetate, cellulose nitrate, polybutylene and ethylene propylene rubber and poly(dimethylsiloxane) (PDMS).

8. The device of claim 1, wherein the protective microporous membrane comprises pores ranging in size from about 5-100 μm.

9. The device of claim 8, wherein the pores range in size from about 10-20 μm.

10. The device of claim 1, wherein the protective microporous membrane is spaced from the exposed surface of the plug surface.

11. The device of claim 1, wherein the stimulus-responsive component comprises a composite of at least one hydrogel that changes porosity when exposed to a stimulus and at least one second polymer or polymer mixture that does not change when exposed to the stimulus.

12. The device of claim 11, wherein the hydrogel is selected from the group consisting of poly(ethylene oxide), polymers of R-acrylamide, R-acrylate or $R_1$-acrylic acid, and $R,R_1,R_2$-cellulose in which R, $R_1$ and $R_2$ may be H, alkyl or —COOH containing groups.

13. The device of claim 11, wherein the second polymer is selected from the group consisting of crosslinked proteins and derivatives thereof, ethylcellulose, methylcellulose, propylcellulose, methoxypropylcellulose, hydroxypropylmethylcellulose, cellulose nitrate, poly(vinyl alcohol), poly(vinyl chloride), polystyrene, polyethylene, polypropylene, poly(ethylene-co-vinyl acetate), polyesters, poly(hydroxybutyric acid), poly(hydroxyvalerianic acid-co-hydroxybutyric acid), poly(lactic acid), poly(glycolic acid), poly(lactic acid-co-glycolic acid), poly(ϵcaprolactones), poly(ϵcaprolactone-co-DL-lactic acid), polyanhydrides, poly(maleic anhydride), polyamides, albumin, gelatin, chitosan, collagen, poly(hydroxyalkyl)-L-glutamines, poly(γ-ethyl-L-glutaminate-co-glutamic acid), poly(L-leucine-co-L-aspartic acid), poly(proline-co-glutamic acid), poly(orthoesters), poly(alkyl 2-cyanoacrylates), polylysine, alginate, alginic acid, polyurethanes, poly(methyl methacrylate), poly(methyl methacrylate-co-methacrylic acid) and poly(methacrylate-co-hydroxypropyl methacrylate).

14. The device of claim 11, wherein the stimulus-responsive component comprises a catalytic component that catalyzes the change in porosity in the hydrogel component in response to a change in the glucose level.

15. The device of claim 14, wherein the catalytic component comprises glucose oxidase that optionally includes catalase.

16. The device of claim 1, wherein the inorganic component comprises one or more of $MnO_2$, Ag, Au, $SiO_2$, titanium, iron, magnesium, silica-based materials and non-hydrocarbon-based nanomaterials.

17. The device of claim 1, wherein the plug comprises the inorganic component in an amount in the range of about 0.01%-25% (w/w).

* * * * *